US011898197B2

(12) United States Patent
Escajeda et al.

(10) Patent No.: US 11,898,197 B2
(45) Date of Patent: *Feb. 13, 2024

(54) SYSTEM AND SELF-METERING CARTRIDGES FOR POINT OF CARE BIOASSAYS

(71) Applicant: WAINAMICS, INC., Pleasanton, CA (US)

(72) Inventors: Arturo M. Escajeda, Oakland, CA (US); Huyen Tran, San Jose, CA (US); Ming X. Tan, San Ramon, CA (US)

(73) Assignee: Wainamics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/016,630

(22) PCT Filed: Jul. 29, 2021

(86) PCT No.: PCT/US2021/043647
§ 371 (c)(1),
(2) Date: Jan. 17, 2023

(87) PCT Pub. No.: WO2022/026670
PCT Pub. Date: Feb. 3, 2022

(65) Prior Publication Data
US 2023/0193366 A1    Jun. 22, 2023

Related U.S. Application Data

(63) Continuation-in-part of application No. 17/158,130, filed on Jan. 26, 2021, and a continuation-in-part of application No. 17/129,783, filed on Dec. 21, 2020.
(Continued)

(51) Int. Cl.
*C12Q 1/6844* (2018.01)
*B01L 3/00* (2006.01)
*B01L 7/00* (2006.01)

(52) U.S. Cl.
CPC ...... *C12Q 1/6844* (2013.01); *B01L 3/502715* (2013.01); *B01L 7/52* (2013.01);
(Continued)

(58) Field of Classification Search
CPC ....... B01L 2300/087; B01L 2200/0605; B01L 3/502715; B01L 2400/049; B01L 2200/16; C12Q 1/6844
See application file for complete search history.

(56) References Cited

U.S. PATENT DOCUMENTS 5,096,669 A    3/1992  Lauks
6,379,929 B1   4/2002  Burns
(Continued)

FOREIGN PATENT DOCUMENTS

WO  WO2016/073415    5/2016
WO  WO2018/175169    9/2018
(Continued)

OTHER PUBLICATIONS

Chen et al, "An integrated, self-contained microfluidic cassette for isolation, amplification, and detection of nucleic acids," Biomed. Microdevices, 12(4): 705-719 (2010).
(Continued)

*Primary Examiner* — Young J Kim
(74) *Attorney, Agent, or Firm* — Stephen C. Macevicz

(57) ABSTRACT

The invention is directed to devices and methods for performing rapid low-cost bioassays in self-contained disposable cartridges that provide efficient mixing of sample and reactants under a layer of liquid wax. Some embodiments additionally use gravity assisted distribution of sample and assay reagents in conjunction with an appliance containing all necessary valves, pneumatic sources, heat sources and detection stations.

10 Claims, 26 Drawing Sheets

Related U.S. Application Data

(60) Provisional application No. 63/058,535, filed on Jul. 30, 2020.

(52) U.S. Cl.
CPC ....... *B01L 2200/04* (2013.01); *B01L 2200/16* (2013.01); *B01L 2300/0654* (2013.01); *B01L 2300/087* (2013.01); *B01L 2300/0883* (2013.01); *B01L 2300/1805* (2013.01); *B01L 2400/049* (2013.01); *B01L 2400/0481* (2013.01); *B01L 2400/0677* (2013.01)

(56) References Cited

U.S. PATENT DOCUMENTS

| | | |
|---|---|---|
| 6,410,278 B1 | 6/2002 | Notomi |
| 7,264,932 B2 | 9/2007 | Latham |
| 8,673,567 B2 | 3/2014 | Wang |
| 9,133,024 B2 | 9/2015 | Phan |
| 9,731,297 B2 | 8/2017 | Glezer |
| 9,797,006 B2 | 10/2017 | Niemz |
| 9,797,899 B2 | 10/2017 | Bornheimer |
| 9,962,698 B2 | 5/2018 | Ingber |
| 10,073,093 B2 | 9/2018 | Bornheimer |
| 10,107,797 B2 | 10/2018 | Battrell |
| 10,807,093 B2 | 10/2020 | Belotserkovsky |
| 2002/0168671 A1 | 11/2002 | Burns |
| 2008/0026451 A1 | 1/2008 | Braman |
| 2008/0182312 A1 | 7/2008 | Pack |
| 2010/0035349 A1* | 2/2010 | Bau ............. G01N 35/0092 422/68.1 |
| 2013/0344563 A1 | 12/2013 | Raines |
| 2015/0125882 A1 | 5/2015 | Bornheimer |
| 2016/0175840 A1 | 6/2016 | Ingber |
| 2018/0016537 A1 | 1/2018 | Levner |
| 2018/0236446 A1 | 8/2018 | Malkin et al. |
| 2019/0232284 A1 | 8/2019 | Travi |
| 2022/0032293 A1* | 2/2022 | Escajeda ........... B01L 3/502715 |
| 2022/0032294 A1* | 2/2022 | Escajeda ............... B01L 7/52 |

FOREIGN PATENT DOCUMENTS

| | | |
|---|---|---|
| WO | WO2022/026670 | 12/2021 |
| WO | WO2022/026670 | 2/2022 |

OTHER PUBLICATIONS

Chin et al, "Commercialization of microfluidic point-of-care diagnostic devices," LabChip, 12: 2118-2134 (2012).
Findlay et al, "Automated closed-vessel system for in vitro diagnostics based on polymerase chain reaction," Clin. Chem., 39(9): 1927-1933 (1993).
Gadkar et al, "Real-time detection and monitoring of loop mediated amplification (LAMP) reaction using self-quenching and de-quenching fluorogenic probes," Scientific Reports, 8:5548 (2018).
Gill et al, "Nucleic acid isothermal amplification technologies," Nucleosides, Nucleotides, and Nucleic Acids, 27: 224-243 (2008).
Goto et al, "Colorimetric detection of loop-mediated isothermal amplification reaction by using hydroxyl naphthol blue," BioTechniques, 46: 167-172 (2009).
Haeberle et al, "Microfluidic platforms for lab-on-a-chip applications," LabChip, 7: 1094-1110 (2007).
Hardinge et al, "Reduced false positives and improved reporting of loop-mediated isothermal amplification using quenched fluorescent primers," Scientific Reports, 9:7400 (2019).
Hitzbleck et al, "Reagents in microfluidics: an 'in' and 'out' challenge," Chem. Soc. Rev., 42: 8494 (2013).
Karami et al, "A review of the current isothermal amplification techniques: applications, advantages and disadvantages," J. Global Infectious Diseases, 3(3): 293-302 (2011).
Kim et al, "Microfluidic sample preparation: cell lysis and nucleic acid purification," Integrative Biology, 1: 574-586 (2009).
Lee et al, "Bubble-free rapid microfluidic PCR," Biosensors and Bioelectronics, 126: 725-733 (2019).
Lochovsky, "Trapping and removal of bubbles in a microfluidic format," Thesis, Institute of Biomaterials and Biomedical Engineering, University of Toronto (2012).
Nge et al, "Advances in microfluidic materials, functions, integration and applications," Chem. Rev., 113(4): 2550-2583 (2013).
Nie et al, "Evaluation of Alere i influenza A&B for rapid detection of influenza viruses A and B," J. Clinical Microbiology, 52(9): 3339-3344 (2014).
Oscorbin et al, "Comparison of fluorescent intercalating dyes for quantitative loop-mediated isothermal amplification (LAMP)" BioTechniques, 61(1): 20-25 (2016).
Periero et al, "Nip the bubble in the bud: a guide to avoid gas nucleation in microfluidics," LabChip, 19: 2296-2314 (2019).
Quyen et al, "Classification of multiple DNA dyes based on inhibition effects on real-time loop-mediated isothermal amplification (LAMP): Prospect for point of care setting," Frontiers in Microbiology, 10:2234, doi: 10.3389/fmich.2019.02234, (2019).
Ren et al, "Materials for microfluidic chip fabrication," Accounts of Chemical Research, 46(11): 2396-2406 (2013).
Smith et al, "Blister pouches for effective reagent storage on microfluidics chips for blood cell counting," Microfluid Nanofluid, 20: 163 (2016).
Svec et al, "Direct cell lysis for single-cell gene expression profiling," Frontiers in Oncology, 3: article 274 (2013).
Zhang et al, "Rapid molecular detection of SARS-CoV-2 (COVID-2) virus RNA using colorimetric LAMP," medRxiv, doi.org/10.1101/2020.02.26.20028373 (Feb. 29, 2020).
Zhu et al, "Development of a new method for turbidity measurement using two NIR digital cameras," ACS Omega, 5: 5421-5428 (2020).

\* cited by examiner

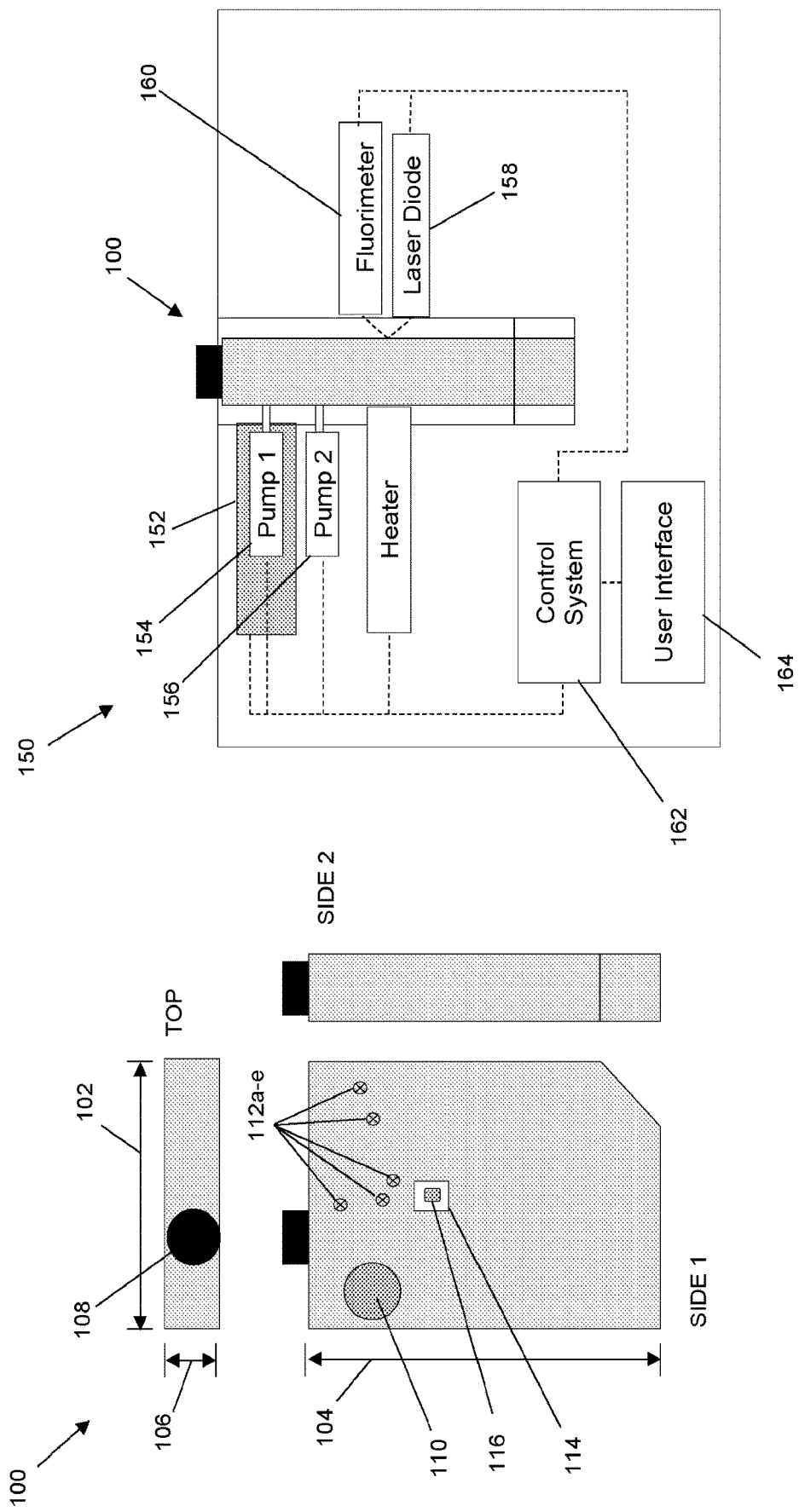

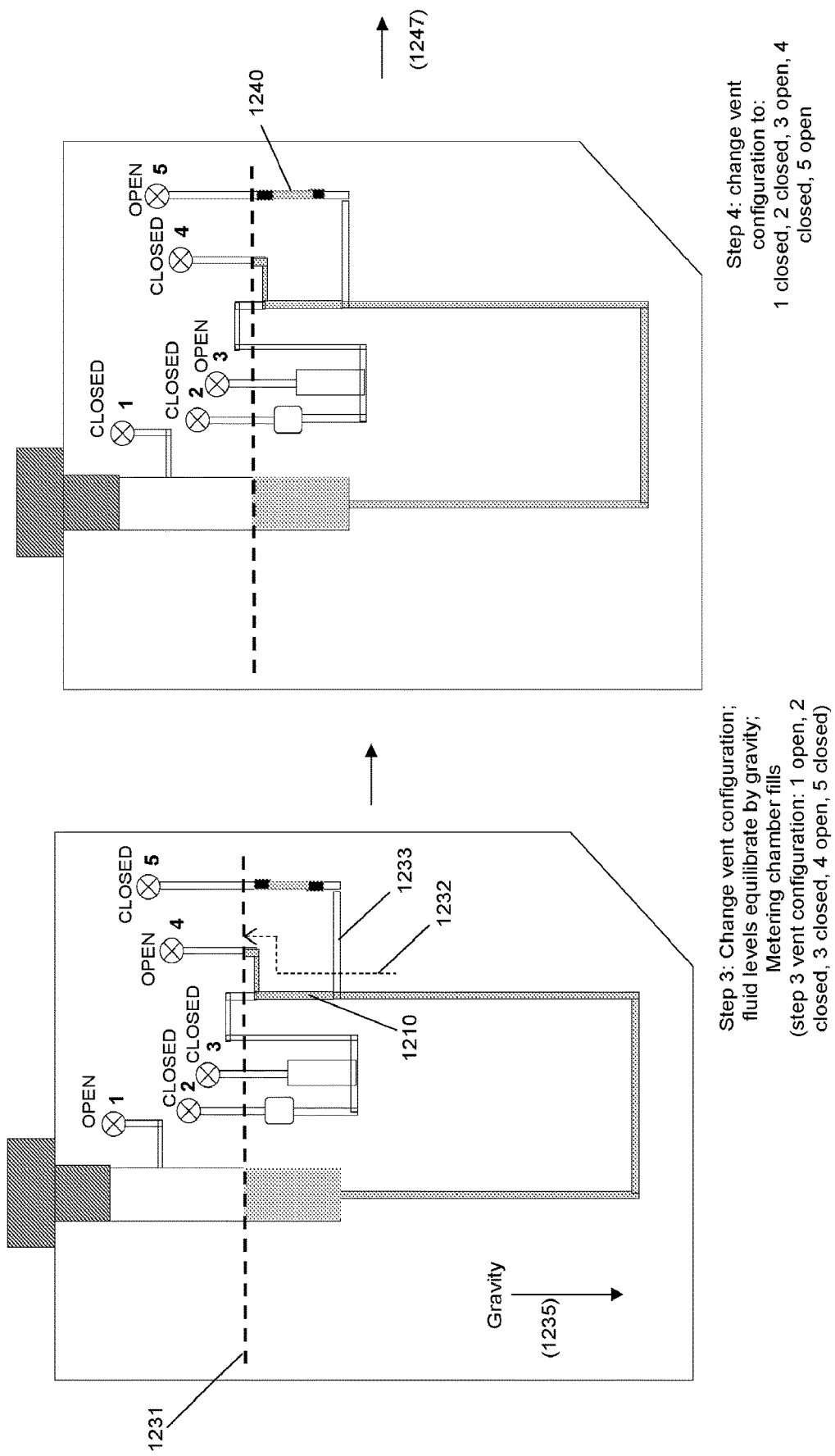

Fluid distribution at the end of step 5: Metered amount of sample and reaction Components in mixing chamber Step 5: Pressure applied through vent 5; Reaction components pushed into mixing chamber Step 8: Assay performed in detection chamber; Readout from appliance Step 7: Vacuum applied to vent 2; reaction mixture drawn into detection chamber

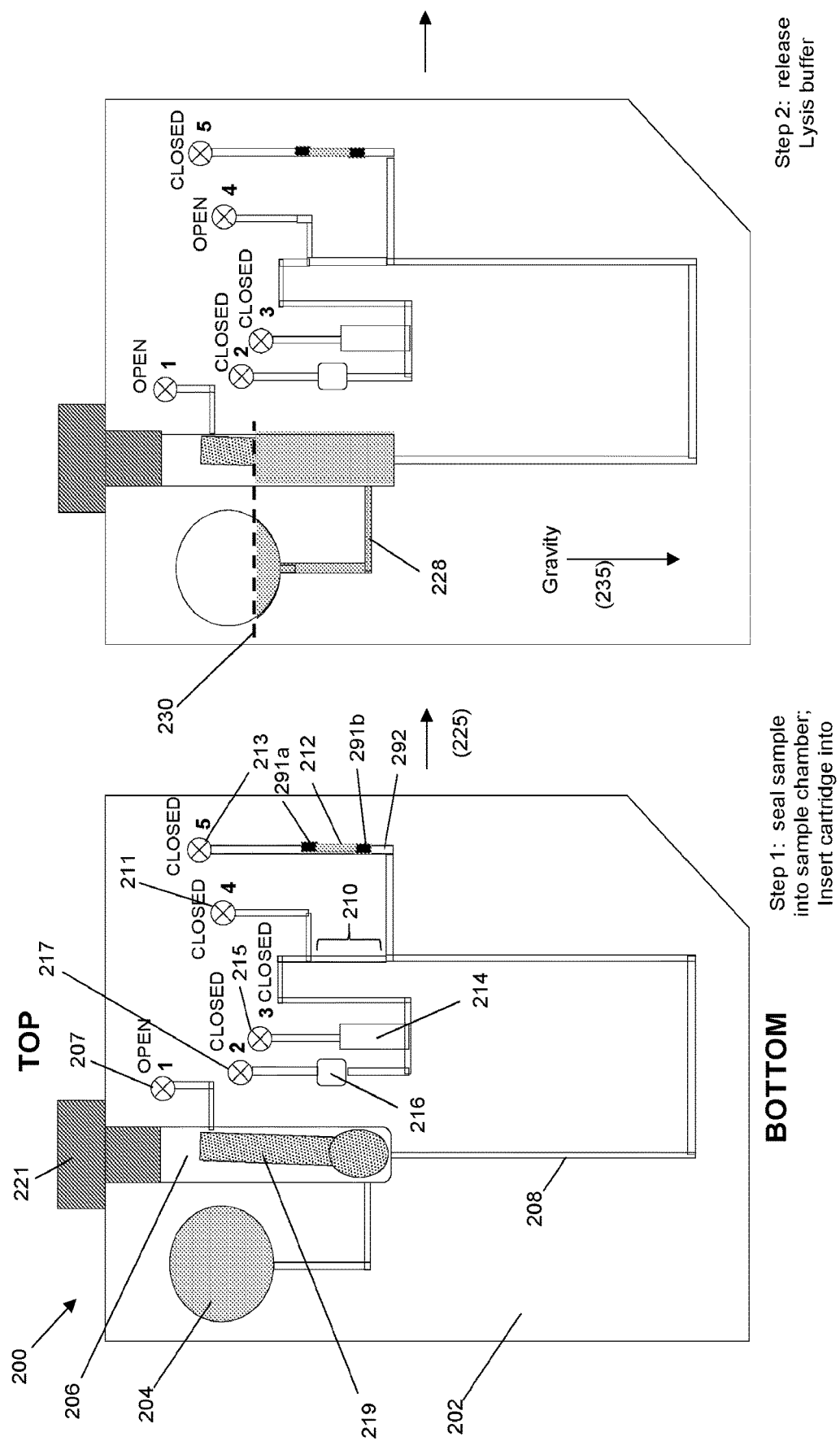

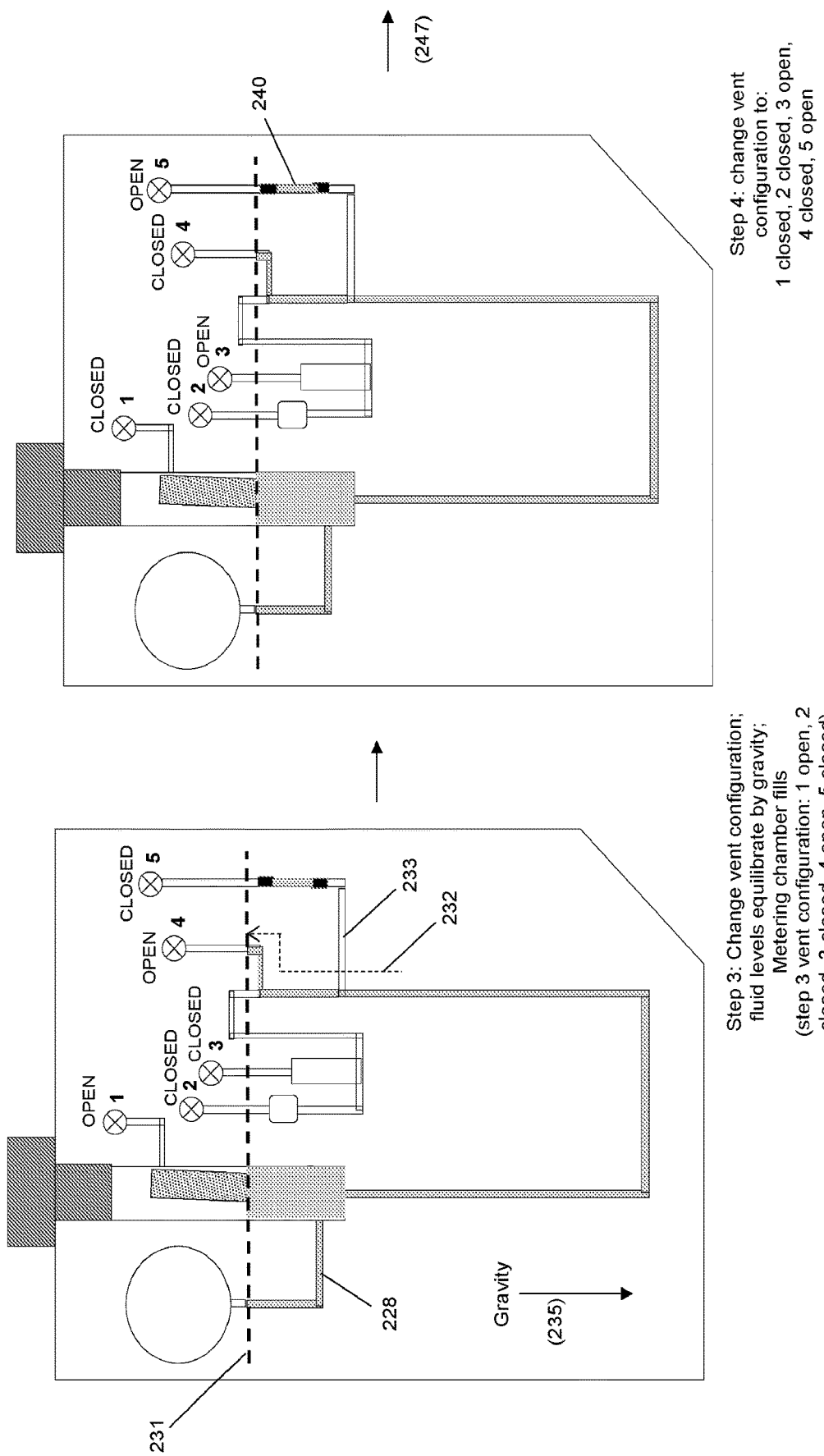

Step 7: Vacuum applied to vent 2; reaction mixture drawn into detection chamber

Step 6: change vent configuration to: 1 closed, 2 open, 3 open, 4 closed, 5 closed

| Port | Open/Close |
|---|---|
| 1 | Open (vent) |
| 2 | Closed |
| 3 | Closed |
| 4 | Closed |
| 5 | Open (vacuum) |

| Port | Open/Close |
|---|---|
| 1 | Closed |
| 2 | Closed |
| 3 | Open (vent) |
| 4 | Open (pressure) |
| 5 | Closed |

| Port | Open/Close |
|---|---|
| 1 | Closed |
| 2 | Closed |
| 3 | Open (vent) |
| 4 | Open (pressure) |
| 5 | Closed |

| Port | Open/Close |
|---|---|
| 1 | Closed |
| 2 | Open (vent) |
| 3 | Open (pressure) |
| 4 | Closed |
| 5 | Closed |

Storage of Lysis Buffer and Nuclease Inhibitors

SYSTEM AND SELF-METERING CARTRIDGES FOR POINT OF CARE BIOASSAYS

This application was filed under 35 USC 1.371(f) based on International Application serial number PCT/US2021/043647 filed 29 Jul. 2021, which claims priority from U.S. nonprovisional application Ser. No. 17/158,130 filed 26 Jan. 2021 and Ser. No. 17/129,783 filed 21 Dec. 2020, and from U.S. provisional application Ser. No. 63/058,535 filed 30 Jul. 2020. Each of the foregoing applications is incorporated herein by reference in its entirety.

In many medical emergencies, such as sudden spread of a highly contagious infectious agent, such as COVID19, the implementation of widespread testing with accurate, easy-to-use rapid and low-cost assays is paramount for assessing and controlling its impact. Real-time PCR tests are highly-sensitive and accurate for assessing viral load. However, these tests have the disadvantage of having high sample preparation and reagent handling requirements and usually require personnel with specialized training. While many companies have launched assay systems that allow for point of care testing, typically they require assay cartridges and instrumentation that are bulky, complex and costly.

It would be highly desirable, especially for medical applications in resource poor settings, if there were available simpler and less costly devices for rapid and effective testing in populations exposed to highly contagious viral diseases.

SUMMARY OF THE INVENTION

The invention is directed to methods, systems and self-metering cartridges, including microfluidic devices, for implementing rapid low-cost point-of-care bioassays, especially nucleic acid based bioassays.

In one aspect, the invention includes a single-use device, or cartridge, for performing a bioassay on a biological sample in order to determine in conjunction with an associated appliance the presence or quantity of one or more biomolecules, such as one or more polynucleotides. The associated appliance is a multi-use device that provides thermal sources, pressure and vacuum sources, mechanical actuators, and a detection station to enable a bioassay on the single-use cartridge. In some embodiments, a cartridge of the invention comprises: a card-like planar body with a top and a bottom, the planar body comprising a sample chamber, optionally a lysis reservoir (or lysis buffer chamber), a first conduit, at least one reagent chamber, at least one metering chamber, at least one mixing chamber and at least one detection chamber, wherein at least one of the one or more reagent chambers or the one or more mixing chambers comprises a predetermined quantity of a wax, which may be employed as a bubble suppressant as described below. An aspect of the invention is the use of a mixing chamber to pneumatically mix assay reagents of a reaction mixture by forcing a gas, e.g. air, into the bottom of the mixing chamber where it passes through the surface of the reaction mixture and is exhausted through a vent port associated with the mixing chamber. Included among the assay reagents is a wax that melts and forms a layer on top of the reaction mixture that prevents the injected gas from forming bubbles at the surface of the reaction mixture or from transporting fluid to the vent port. In some embodiments, a layer of wax having a thickness of from about 100 µm to 1-2 mm is sufficient for suppressing bubble formation. Thus, depending on particular embodiments, a predetermined quantity of wax is selected to provide a layer of wax over a reaction mixture with a thickness in such range. In some embodiments, whenever a reaction mixture has a volume in the range of from 30-50 µL a volume of 10 µL of wax may be employed. In some embodiments, the wax barriers, and optionally a predetermined quantity of wax in the mixing chamber, are melted to form a bubble-preventing layer on a reaction mixture, after which the reaction mixture is transferred to the detection chamber for performance of a bioassay.

In some embodiments, during operation the top and the bottom of a cartridge is aligned with the direction gravity; or, in other words, in operation, a cartridge is oriented vertically with its top uppermost. Such orientation permits released reagents to fill predetermined chambers under the force of gravity.

In some embodiments, a biological sample is inserted directly into the sample chamber. For example, a biological sample may be on or in a swab used to collect the biological sample and the swab may be placed directly into the sample chamber. In other embodiments, a biological sample may be collected and undergo one or more processing steps before insertion into the sample chamber. Such preparations may include mixing or exposing the biological sample to various extraction procedures, including exposure to heat or extraction reagents, such as beads, or to a lysis buffer, all of which serve to release target biomolecules into a sample fluid which is more amenable for analysis by a bioassay. As used herein, "sample fluid" means a fluid containing biomolecules of interest. A sample fluid may be generated in a cartridge by incubating a biological sample with a lysis buffer or other reagents, or a sample fluid may be generated separate from a cartridge and later inserted into a sample chamber of the cartridge (or planar body). In some embodiments, sample preparation could also be implemented in a separate sample preparation cartridge, where a sample is heated, mixed with beads for DNA/RNA sample lysing and extraction. Sample preparation could also include a device where multiple samples are pooled into a single sample for extraction so that multiple assays are tested at the same time.

In some embodiments, the sample chamber has oblong dimensions with a top and a bottom in the same orientation as the top and bottom of the planar body and has a first inlet at its top for accepting a biological sample, a lid for sealing the first inlet after a biological sample is inserted, a vent port at its top allowing the passage of air but not liquid, and an outlet at its bottom connected to a first conduit. The vent port is capable of being sealingly connected to a valve in the appliance.

In some embodiments, the optional lysis reservoir contains a predetermined quantity of lysis buffer that is capable of being released through a passage connected to the second inlet of the sample chamber.

In some embodiments, the metering chamber has a top and a bottom in the same orientation as the top and bottom of the planar body such that the bottom of the metering chamber is (i) connected to the reagent chamber and (ii) connected to and in fluid communication with the outlet of the sample chamber through the first conduit and such that the top of the metering chamber is (iii) connected to a metering vent port and (iv) connected to a mixing chamber conduit, wherein the top of the metering chamber is positioned in the planar body at a predetermined distance above the bottom of the sample chamber so that whenever the lysis buffer is released into the sample chamber it is capable of flowing through the first conduit to the top of the metering chamber upon reaching an equilibrium level under gravity, thereby introducing a predetermined amount of lysis buffer into the metering chamber. The metering vent port is capable of being sealingly connected to a valve in the appliance. In some embodiments, one or more filters may be disposed in, or in series with, the first conduit, for example, to prevent undesirable debris from entering the metering chamber or other passages where it may cause clogging or obstruction.

In some embodiments, the reagent chamber contains assay reagents for performing the analytical reaction and is connected to the bottom of the metering chamber by a passage and connected to a reagent vent port allowing the passage of air but not liquid. The the reagent vent port is capable of being sealingly connected to a valve and pump in the appliance so that the reagent port is capable of accepting air pressure for forcing the assay reagents into the bottom of metering chamber. In some embodiments, a cartridge may comprise multiple reagent chambers either in series or in parallel, which may be delivered simultaneously to a mixing chamber (by forcing reagents of serially connected reagent chambers into the mixing chamber) or which may be delivered in sequence to a mixing chamber (by separately forcing reagents of the parallel chambers). In some embodiments, one-use valves, e.g. a wax barrier or a hydrogel barrier, may be used to isolate the bioassay reagents for storage before use. In some embodiments, such as those using dried reagents disposed in the mixing chamber, a reagent chamber may contain only a solvent, e.g. a buffer solution, which may be moved into the mixing chamber to reconstitute dehydrated assay reagent prior to performing an assay. Likewise, in other embodiments, a subset of assay reagents may be disposed in the reagent chamber and another subset of assay reagents may be disposed in the mixing chamber.

In some embodiments, the first conduit is a passage connecting the outlet of the sample chamber to the bottom of the metering chamber and is in fluid communication with the passage connecting the reagent chamber to the bottom of the metering chamber, wherein fluid occupying the first conduit has a fluid resistance such that whenever pressure is applied to the reagent chamber from the reagent vent port a flow of reagents from the reagent chamber move substantially only into the metering chamber.

In some embodiments, the mixing chamber allows for mixing of the lysis buffer with the assay reagent(s). The mixing chamber has a top and a bottom in the same orientation as the top and bottom of the planar body and is in fluid communication with the metering chamber by a passage connecting the bottom of the mixing chamber to the top of the metering chamber, so that fluid flowing from the metering chamber fills the mixing chamber from bottom to top. The mixing chamber is also connected at its top to a mixing vent port that allows the passage of air but not liquid. The mixing vent port is capable of being sealingly connected to a valve in the appliance.

In some embodiments, the detection chamber has a top and a bottom in the same orientation as the top and bottom of the planar body and is in fluid communication with the mixing chamber by a passage connecting the bottom of the detection chamber to the bottom of the mixing chamber. The detection chamber is also connected at its top to a detection vent port that allows the passage of air but not liquid, wherein the detection vent port is capable of being sealingly connected to a valve and vacuum source in the appliance so that the detection port is capable of accepting a vacuum for drawing the mixture of assay reagents and lysis buffer into the bottom of detection chamber from the mixing chamber.

As explained more fully below, once a cartridge is loaded with a sample and operationally inserted into an appliance, a series of steps are implemented for releasing a lysis buffer (and optionally other reagents, such as nuclease inhibitors), incubating the sample in lysis buffer, metering a quantity of lysis buffer containing released biomolecules by re-configuring vent ports to allow a predetermined equilibrium level of lysis buffer to be established under gravity in the cartridge, forcing reagent to flow through the metering chamber to push a metered amount of lysis buffer with target biomolecules into the mixing chamber to mix with bioassay reagents to form a reaction mixture; forcing the reaction mixture into the detection chamber, performing the bioassay, and detecting a signal to indicate a presence or quantity of a biomolecule.

In some embodiments, the invention comprises a device for performing a bioassay on a biological sample (or a sample prepared from a biological sample (i.e. a sample fluid)) to determine the presence or quantity of one or more target polynucleotides when connected to an appliance that provides pressure sources, vacuum sources, temperature regulation and a detection station. In such embodiments, the device may comprise a planar body comprising a sample chamber, a first conduit, at least one reagent chamber, at least one metering chamber, at least one mixing chamber and at least one detection chamber, wherein: (a) the sample chamber has a first inlet for accepting a biological sample or a sample fluid containing a biological sample, a vent port allowing the passage of air but not liquid, and an outlet connected to a first conduit, wherein the vent port is capable of being sealingly connected to a valve in the appliance; (b) the metering chamber is (i) connected to and in fluid communication with a reagent chamber, (ii) connected to and in fluid communication with the outlet of the sample chamber through the first conduit, (iii) connected to a metering vent port, and (iv) connected to and in fluid communication with a mixing chamber conduit, wherein the metering vent port is capable of being sealingly connected to a valve in the appliance; (c) the reagent chamber is capable of containing assay reagents, the reagent chamber being connected to the metering chamber by a passage and connected to a reagent vent port allowing the passage of air but not liquid, wherein the reagent vent port is capable of being sealingly connected to a valve and pump in the appliance so that the reagent port is capable of accepting air pressure for forcing the assay reagents into the metering chamber; (d) the mixing chamber accepts the biological sample or sample fluid and the assay reagents for mixing, the mixing chamber having a top and a bottom and being in fluid communication with the metering chamber by a passage connecting the bottom of the mixing chamber to the metering chamber, the mixing chamber being connected at its top to a mixing vent port that allows the passage of air but not liquid, wherein the mixing vent port is capable of being sealingly connected to a valve in the appliance, wherein the mixing chamber or the reagent chamber or both chambers contain a predetermined quantity of wax having a melting temperature such that the wax forms a bubble-preventing layer on a reaction mixture whenever the mixing chamber is above the melting temperature; and (e) the detection chamber is in fluid communication with the mixing chamber by a passage connecting the detection chamber at the bottom of the mixing chamber, and the detection chamber is connected at its top to a detection vent port that allows the passage of air but not liquid, wherein the detection vent port is capable of being sealingly connected to a valve and vacuum source in the appliance so that the detection port is capable of accepting a vacuum for drawing the mixture of assay reagents and biological sample or sample fluid into the detection chamber from the mixing chamber. In some embodiments, the assay reagents may be immobilized in the reagent chamber by wax barriers comprising the wax described above, and wherein the assay reagents and the wax barriers are capable of being released upon heating the reagent chamber to a temperature above said melting temperature of said wax. In some embodiments, the target polynucleotides are amplified in an amplification chamber prior to being detected in said detection chamber. In some embodiments, the mixing chamber may be used as an amplification chamber in addition to its mixing function.

In part the invention is a recognition and appreciation that a layer of liquid wax on a reaction mixture can prevent bubbles from forming on the reaction mixture, which otherwise may block a vent through which air must pass to move the reaction mixture into a detection chamber.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTION OF THE DRAWINGS

FIGS. 1A-1B illustrate diagrammatically the basic design of one embodiment of a cartridge and appliance of the invention.

FIGS. 1C-1J exemplify the operation of an embodiment of the invention.

FIGS. 2A-2I exemplify the operation of one embodiment of the invention with on-board sample preparation.

DETAILED DESCRIPTION OF THE INVENTION

Figure 1D:
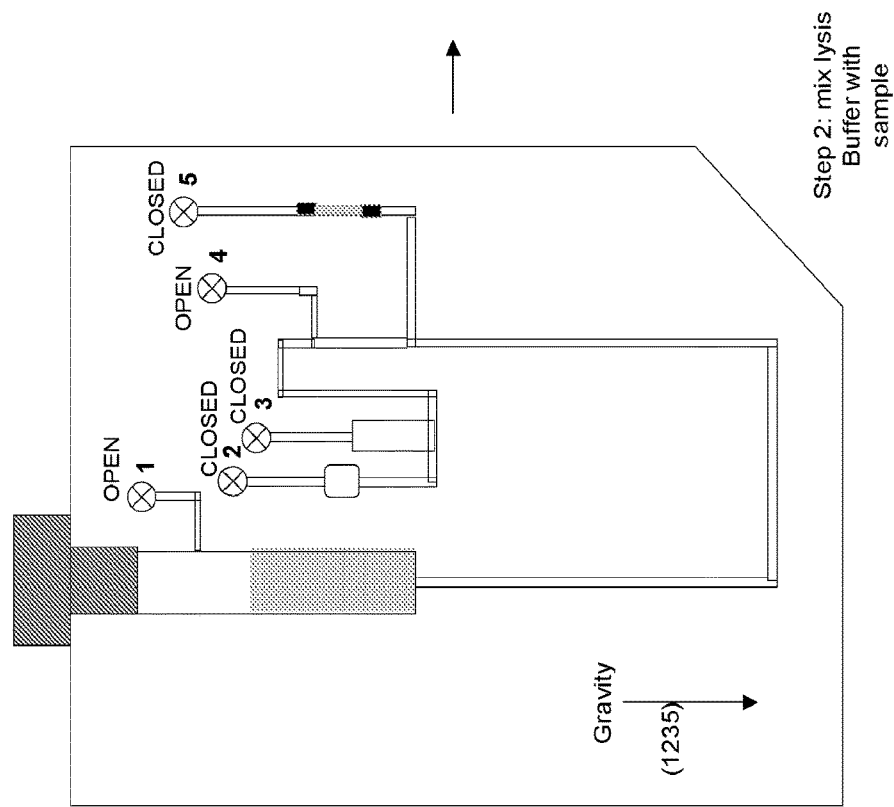

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention. Guidance for selecting materials and components to carry out particular functions may be found in available treatises and references on scientific instrumentation including, but not limited to, Moore et al, Building Scientific Apparatus, Third Edition (Perseus Books, Cambridge, MA); Hermanson, Bioconjugate Techniques, 3rd Edition (Academic Press, 2013); and like references.

The invention is directed to systems for rapid point-of-care bioassays comprising a low-cost disposable assay cartridge and an appliance into which the cartridge may be inserted and operationally connected to provide external physical motive forces (e.g. pressure or vacuum sources, agitation, or the like), heat sources, and detection and readout systems for the bioassays performed in the cartridges. By such connections to the appliance, the need to provide cartridges with on-board valves, pumps, independent power sources, or the like, is reduced or obviated, thereby drastically reducing manufacturing costs. Moreover, in some embodiments, after a sample is inserted and sealed in a cartridge no further physical transfer of liquid material into or out of the cartridge is possible, so that cartridges of the invention are particularly well-suited for bioassays of infectious materials. A feature of some embodiments of the cartridges (when inserted into an appliance) is that components (i.e. passages, chambers and vent ports) are spatially arranged so that a released lysis buffer reaches a predetermined level in the cartridge under gravity and the predetermined level is selected to ensure that each metering chamber is entirely filled with lysis buffer (containing the biomolecule of interest if present in the sample).

Another feature of the invention is the use of a wax initially disposed in solid form in the reaction mixture or the mixing chamber to suppress, after melting, the formation of bubbles in the mixing chamber. A large variety of waxes or comparable compounds, such as silicon oils, may be employed in the invention for this purpose. As used herein the term "wax" means any compound having properties that include (but are not limited to) (a) a melting temperature above or below the freezing point of aqueous reaction mixtures of the bioassays employed, (b) immiscible with aqueous solutions, (c) less dense than the aqueous reaction mixtures, (d) capable of adhering to passage walls and forming leak-proof seals, for example, in passages, to prevent mixing of reagents before melting, (e) compatibility with bioassay chemistry, and (f) ease of handling and manufacturability for facile assembly of disposable cartridges. In some embodiments, a predetermined melting temperature may be in the range of from −50 to 50° C. As mentioned above, a wide variety of compounds and mixtures of compounds may be used as waxes in the invention. In some embodiments, waxes of the invention are alkane based. In some embodiments, waxes may be straight chain or branched chain alkanes and may be used in pure form or as mixtures of more than one alkane. In some embodiments, waxes may comprise $C_{15}$ to $C_{20}$ alkanes. In some embodiments, waxes may comprise commercial parafins. In other embodiments, a wax of the invention may comprise one or more straight chain or branched alkanes having from 15 to 20 carbon atoms. Exemplary waxes include hexadecane, heptadecane, octadecane, nonadecane, icosane, and the like. In some embodiments, a wax used in the invention may comprise mixtures of different compounds selected for tailoring properties of a resulting wax to a particular cartridge embodiment.

As used herein, the term "bioassay" or "assay" means any assay to detect or measure the quantity of a biomolecule. Exemplary biomolecules that may be detected or measured include deoxyribonucleic acids (DNAs), ribonucleic acids (RNAs), proteins, peptides, polysaccharides, lipids, and the like. Further exemplary biomolecules include genes, gene fragments, messenger RNAs (mRNAs), hormones, vitamins, enzymes, coenzymes, immunoglobulins, and the like, e.g. Lehninger, Biochemistry, $2^{nd}$ Edition (Worth Publishers, 1971). In some embodiments, a bioassay is an assay to detect or measure the quantity of a polynucleotide. In some embodiments, a bioassay comprises a polynucleotide amplification. In some embodiments, a bioassay comprises separate polynucleotide amplification and detection steps. Accordingly, in some embodiments, devices of the invention may include an amplification chamber in which one or more target polynucleotides are amplified and a separate detection chamber in which signals are generated for detection or measurement of the target polynucleotides. Such detection may take place in the same chamber as the amplification, or in a different chamber, or chambers. In some embodiments, such bioassays that include a polynucleotide amplification also include an optical readout, e.g. fluorescence intensity, which is monotonically related to the degree of amplification. In some embodiments, such optical readout is a fluorescent signal. In some embodiments, a bioassays is an isothermal polynucleotide amplification assay.

In one aspect, the invention provides cartridges that (i) accept a biological sample, (ii) contain reagents (e.g. lysing reagents or buffers) that release biomolecules of interest from the biological sample, (iii) bioassay reagents to mix with the release biomolecules and to carry out a bioassay designed to detect the presence or a quantity of the biomolecules present. In some embodiments, cartridges of the invention use gravity to redistribute a released lysis buffer in the cartridges, which thereby exposes the biological sample to the lysis buffer and fills a metering chamber with a predetermined quantity of lysis buffer with the released biomolecules. In some embodiments, such predetermined quantity of lysis buffer is in the range of from 100 µL to 1 mL, or in the range of from 200 µL to 500 µL. Bioassay reagents contained in a cartridge are driven by pressure from the appliance with the contents of the metering chamber into a mixing chamber and then to a detection chamber for performance of the bioassay.

An exemplary cartridge and appliance of the invention for detecting a polynucleotide using an isothermal amplification bioassay are illustrated in FIGS. 1A-1B. The dimensions of a cartridge depends in part on the complexity of fluidic movements required to conduct the bioassay. For example, in some embodiments multiple different bioassays may be carried out on different biomolecules from the same sample, or a single bioassay may be carried out on multiple different species of a single type of biomolecule, e.g. multiple species of DNA or RNA. In some embodiments, target polynucleotides may all be amplified in an amplification chamber prior to detection or quantification of some or all the target polynucleotides in the same chamber as the one in which amplification took place. In other embodiments, detection or quantification of the amplified target polynucleotides may take place in a chamber different from the amplification chamber. In still other embodiments, detection or quantification of the amplified target polynucleotides each takes place in a different chamber (for example, after separate amplification). In some embodiments, detection or quantification may require reagents (i.e., "detection reagents") different from the reagents used in an amplification reaction. Thus, in some embodiments, there may be multiple reagent chambers, for example, one reagent chamber for holding amplification reagents and another reagent chamber for holding detection reagents. Thus, a larger cartridge body is required to accommodate multiple reagent, metering, mixing, amplification, detection chambers, and their connecting passages. Likewise, an appliance may require more valves, pumps, thermal cycling stations, and detection stations for detecting or measuring a plurality of different biomolecule in accordance with the invention. FIG. 1A depicts an exemplary cartridge (100) for carrying out a bioassay for a single biomolecule, such as a DNA or RNA. In some embodiments, dimensions of such a cartridge may in the range of from 1-4 cm width (102), 2-8 cm height (104) and 0.5-1 cm depth (106). Typically, cartridges of the invention have a single sample chamber with an opening at the top of the cartridge design to receive a sample, after which the opening is capped with cap (108) to form a liquid-tight seal. Cartridges of the invention have multiple ports that establish pneumatic, optical and physical connections with an appliance. For example, after insertion of cartridge (100) into appliance (150) (shown in FIG. 1B) side 1 of cartridge (100) includes blister pouch (or pack) (110) that aligns with actuator (152) (behind pump 1), vent ports (112a, 112b, 112c, 112d, 112e) two of which (identified in FIGS. 2A-2D) align with pump 1 (154) and pump 2 (156) and the rest of which (identified in FIGS. 2A-2D) align with valves that open or close either to allow air passage through the vent ports or to block air passage through the vent ports. In some embodiments, vent ports may align and sealingly connect with a three-way valve having a passage that leads to a pump, a passage that leads to a vent, and a passage that leads to the cartridge. Window (114) that aligns with laser diode (158) and fluorometer (160) permits optically based detection or measurement of a signal from detection chamber (116) of cartridge (100). Thermal source (161) maintains the detection chamber at a predetermined temperature in the case of an isothermal bioassay or thermal cycles a reaction mixture in the detection chamber in the case of, for example, a real time PCR. Appliance (150) further includes control system (162) comprising a computer for controlling (i) initiation of lysis buffer release, e.g. by having actuator (152) rupture blister pouch (110), (ii) actuation of pumps and valves, (iii) actuation of the signal detection components, (iv) collection and storage of data, (v) transmitting bioassay results to the user, e.g. via user interface (164).

In some embodiments, an appliance may also include a heating or thermal control component for maintaining either a detection chamber a predetermined temperature, e.g. for an isothermal amplification assay, or for cycling an amplification chamber among several temperatures, e.g. for performing a polymerase chain reaction. In embodiments employing an isothermal bioassay, a predetermined temperature in the range of from 55° C. to 70° C. is employed, and in some embodiments, a predetermined temperature in the range of from 60° C. to 65° C. is employed. For a bioassay employing CRISPR-based detection, a detection chamber may be held in a predetermined temperature in the range of from 30° C. to 60° C.; or in some embodiments, a predetermined temperature in the range of from 32° C. to 40° C. Additional heating units may be deployed to heat the reagent chamber to melt wax barriers for releasing assay reagents or to heat the mixing chamber to maintain the wax in a melted state.

Figure 1C:
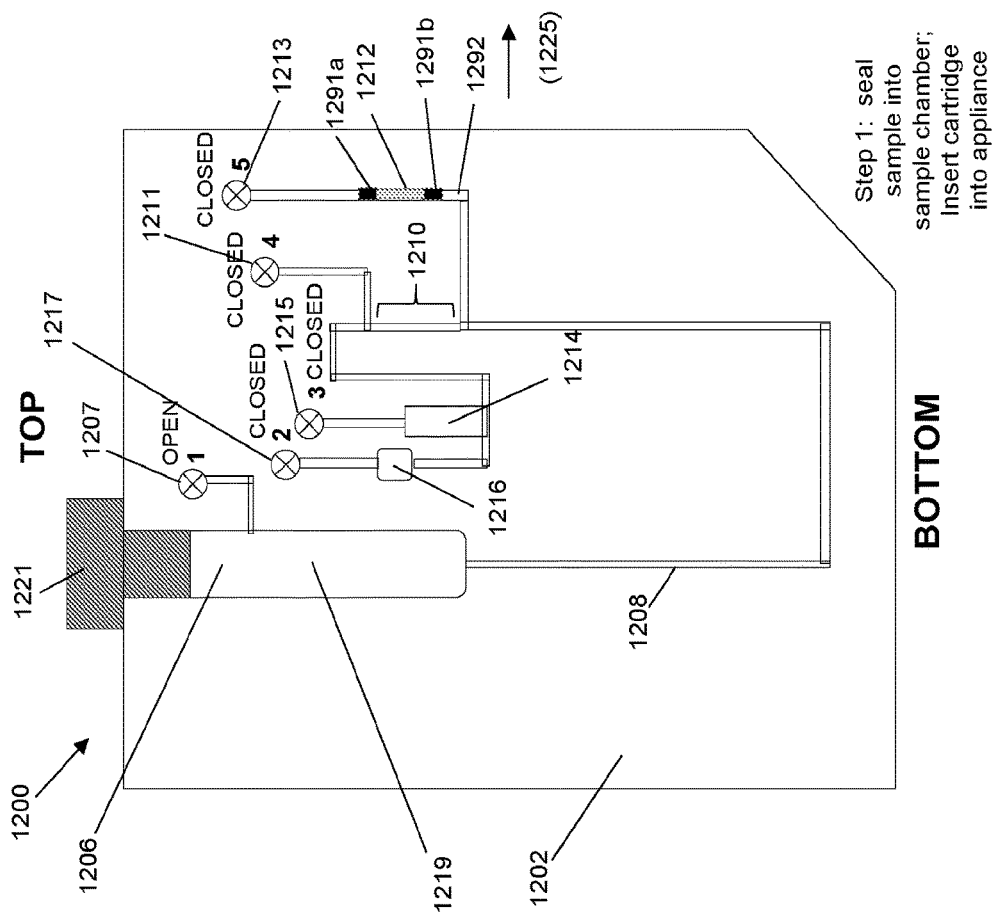

FIGS. 1C-1J illustrate the operation of an embodiment of the invention for performing an isothermal amplification and detection of a target nucleic acid wherein sample preparation, i.e. generating a sample fluid, is carried out off-cartridge. That is, a sample fluid is prepared separately from the cartridge, then inserted into the sample chamber of the cartridge. In FIG. 1C, cartridge (1200) comprises body (1202) with sample chamber (1206) with cap (1221), vent port 1 (1207), first conduit (1208), metering chamber (1210) with vent port 4 (1211), reagent chamber (1212) with vent port 5 (1213), mixing chamber (1214) with vent port 3 (1215), and detection chamber (1216) with vent port 2 (1217). In some embodiments, sample chamber (1206) may also comprise a filter at its bottom outlet to prevent particulate matter from entering first conduit (1208) and other passages where they may cause obstructions. After inserting or loading a predetermined volume of sample fluid and sealing sample chamber with cap (1221), vent ports 1-5 (1207, 1217, 1215, 1211, and 1213, respectively) are configured as follows (wherein "closed" means no liquid and no air passes through the vent port, and "open" mean no liquid but air may pass through the vent port):

| Starting Vent Port Configuration | |
|---|---|
| Vent Port No. | Open/Closed |
| 1 | OPEN |
| 2 | CLOSED |
| 3 | CLOSED |
| 4 | CLOSED |
| 5 | CLOSED |

With this configuration sample fluid (illustrated by gray shading) remains in sample chamber (1206). After loading, the valve states are changed to the following configuration:

| Second Vent Port Configuration | |
|---|---|
| Vent Port No. | Open/Closed |
| 1 | OPEN |
| 2 | CLOSED |
| 3 | CLOSED |
| 4 | OPEN |
| 5 | CLOSED |

The above configuration allows sample fluid (illustrated by gray shading) to move by the force of gravity (1235) from sample chamber (1206) through first conduit (1208), through metering chamber (1210) and towards (1232) open vent port (1211). Sample fluid does not move towards vent ports 2 (1217), vent port 3 (1215) or vent port 5 (1213) because each of these are closed or in the case of vent port 5 (1213), passage (1233) is obstructed by bioassay reagents in reagent chamber (1212). As illustrated in this figure, reagent chamber (1212) is formed by disposing wax barriers (1291*a* and 1291*b*) upstream and downstream of the assay reagent in passage (1292). In some embodiments, the passage (1233) may be blocked with a low-melting point wax or hydrogel. Also, in some embodiments, one or more, or all, bioassay reagents may be stored in a blister pouch that releases the bioassay reagents by mechanical actuation. After the sample fluid is released as illustrated it reaches a second predetermined equilibrium level (1231) that is above the top outlet of metering chamber (1210). The amount of sample fluid (i.e., the predetermined volume), the sizes and the positions in body (1202) of sample chamber (1206) and metering chamber (1210) are selected so that the predetermined equilibrium level (1231) is above the top outlet of metering chamber (1210).

From predetermined equilibrium level (1231), as illustrated in FIGS. 1E and 1F, and the vent port configuration is changed as follows:

| Third Vent Port Configuration | |
|---|---|
| Vent Port No. | Open/Closed |
| 1 | CLOSED |
| 2 | CLOSED |
| 3 | OPEN |
| 4 | CLOSED |
| 5 | OPEN |

Figure 1H:
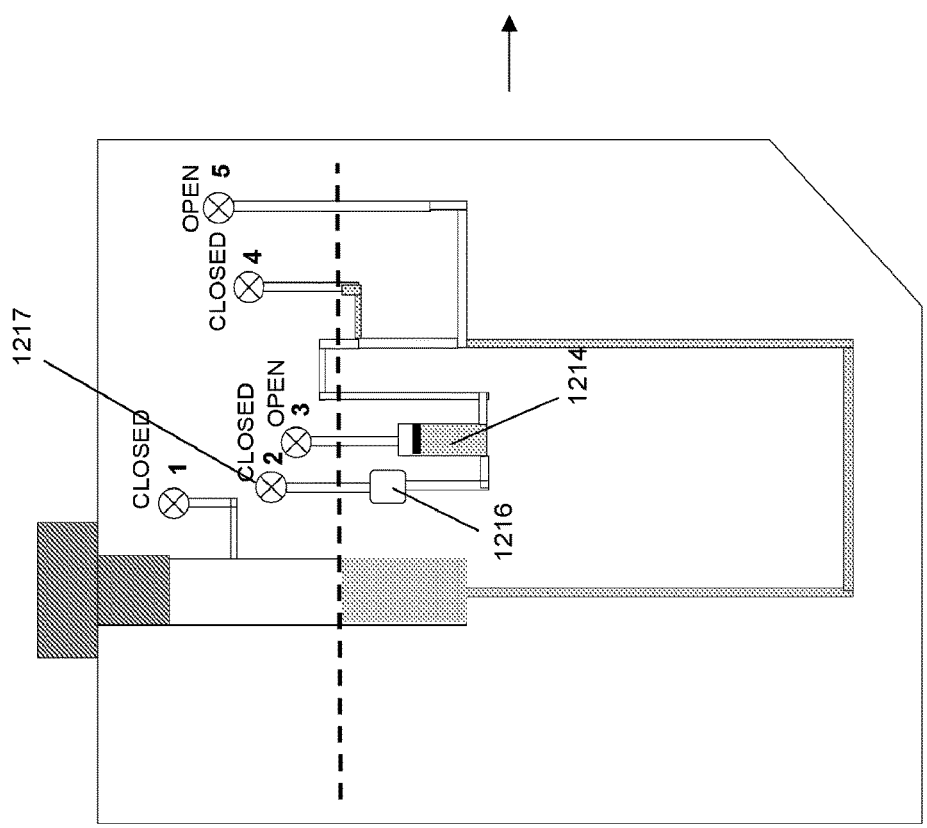
Figure 1G:
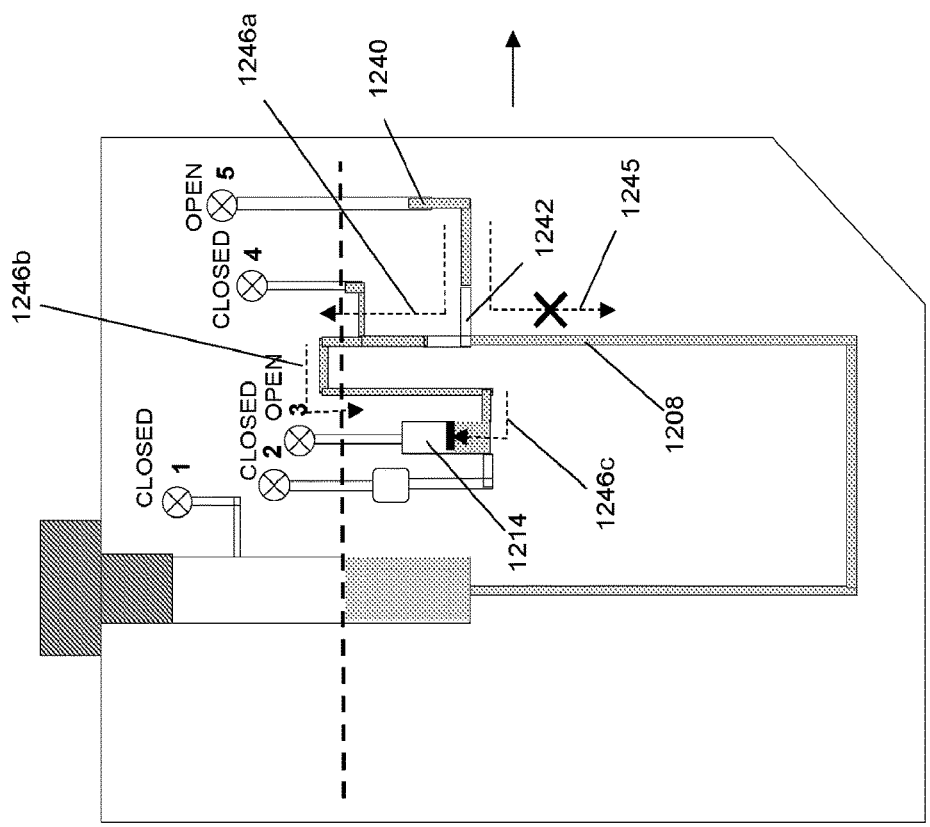

As illustrated in FIG. 1G, in this configuration pressure is applied through vent port 5 (1213) to force bioassay reagents in reagent chamber (1212) to flow through passages indicated by arrows (1246*a*, 1246*b* and 1246*c*) and into mixing chamber (1214). Vent port 5 (1213) is operationally associated with pump 2 (156, FIG. 1B) which generates pressure at vent port 5 upon receiving an actuation signal from control system (162, FIG. 1B), e.g. by moving a piston in pump 2 a predetermined amount. Bioassay reagent (1240) does not flow through first conduit (1208) as indicated by arrow (1245) because first conduit is designed (by selecting length, cross-section, degree of crenulation, and like parameters) to present fluid resistance to such flow. In some embodiments, first conduit (1208) is designed to have a zig-zag pattern and a length which is sufficient to block any substantial flow of bioassay reagent into first conduit (1208). The step of forcing bioassay reagent (1240) and the metered amount of sample fluid into mixing chamber (1214) allows any bubbles (1242) in the line to be removed before transferring the mixture to a temperature cycling chamber or directly to detection chamber (1216). FIG. 1H illustrates the distribution of sample fluid and reaction mixture in cartridge (1200) after the bioassay reagents and metered sample have been forced into mixing chamber (1214).

Although the cartridge of FIGS. 1C-1J show the bioassay reagent being held in a single reagent chamber (1212) directly connected to first conduit (1208) and metering chamber (1210), in some embodiments, there may be multiple reagent chambers that hold different components for a bioassay, for example, primers in one compartment and polymerase in another compartment. Such compartments may be arranged in serial fashion, so that the components are stored separately, but that an application of pressure forces all components to flow through the same passage to mixing chamber (1214) for mixing. Alternatively, multiple components can each be stored separately in parallel branches each with a single reagent chamber connected at one end to first conduit (1208) and metering chamber (1210) and connected at the other end a vent port operationally associated with a pump or other pressure source. In the latter, embodiment, bioassay reagents may be delivered independently to mixing chamber (1214) or to a temperature cycling chamber or detection chamber (1216). In both alternatives, bioassay reagents may be further isolated by sealing inlet and outlet passages with a wax, hydrogel, or like obstruction, that can be removed by heating from an appliance.

Returning to FIG. 1H, after step 5 (that is, after sample fluid, biomolecules of interest, and bioassay reagents are mixed to form a reaction mixture in mixing chamber (1214)), the vent configuration is changed to permit reaction mixture in mixing chamber (1214) to be pulled into detection chamber (1216) by applying vacuum to vent port 2 (1217). There are several alternative vent port configurations which will allow such transfer. Namely, vent port 2 (1217) is open and any one or all of the vent ports 1, 3, 4 and/or 5 may be open. In some embodiments, the following vent port configuration is employed in step 5:

| Fourth Vent Port Configuration (1$^{st}$ alternative) | |
| --- | --- |
| Vent Port No. | Open/Closed |
| 1 | CLOSED |
| 2 | OPEN |
| 3 | OPEN |
| 4 | CLOSED |
| 5 | CLOSED |

In some embodiments, the following alternative vent port configuration may be employed:

| Fourth Vent Port Configuration (2$^{nd}$ alternative) | |
| --- | --- |
| Vent Port No. | Open/Closed |
| 1 | OPEN |
| 2 | OPEN |
| 3 | CLOSED |
| 4 | CLOSED |
| 5 | CLOSED |

Figure 1J:
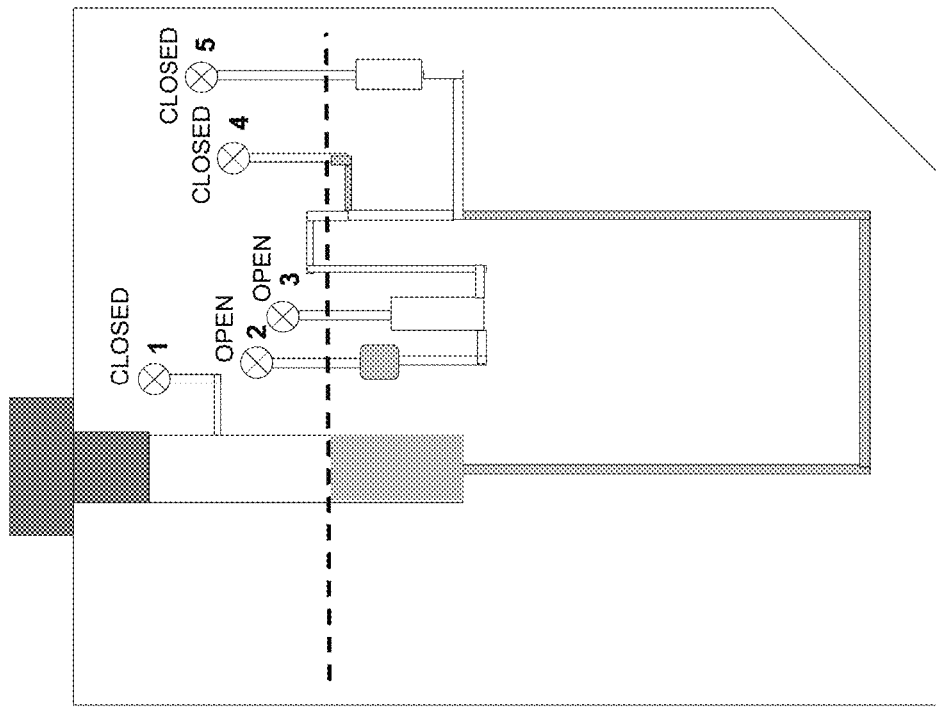
Figure 1I:
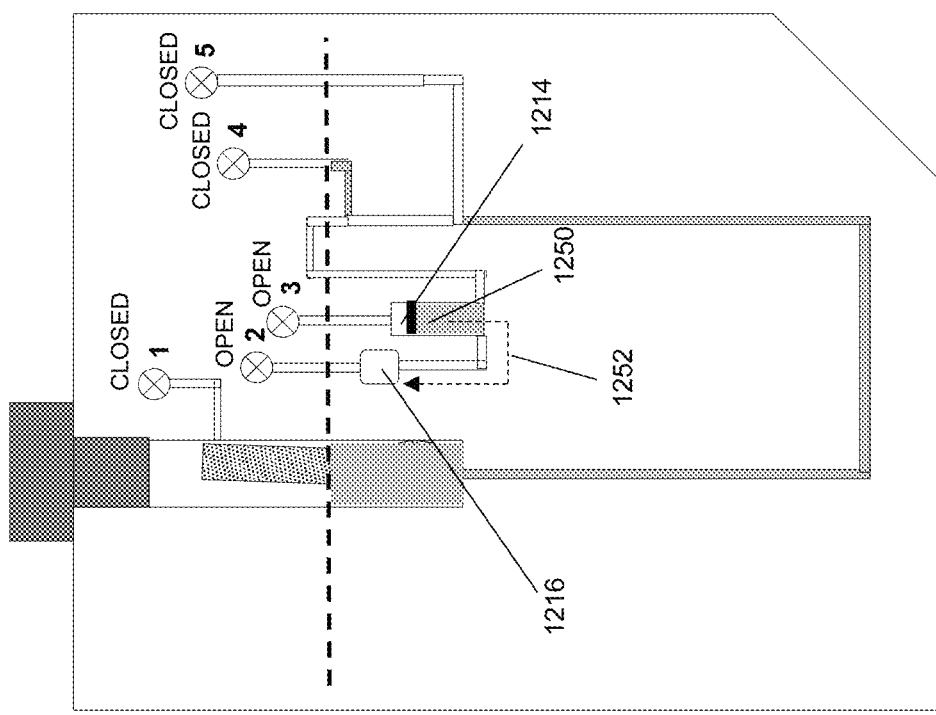

As illustrated in FIG. 1I, employing the first alternative vent port configuration, upon application of vacuum to vent port 2, reaction mixture (1250) is pulled from mixing chamber (1214) into detection chamber (1216), as indicated by arrow (1252), to give the final distribution of sample fluid and reaction mixture (1250) as shown in FIG. 1J. Whenever the biomolecule of interest is a polynucleotide and its detection is based on an isothermal reaction, in the illustrated embodiment, no further movement of liquid is necessary. At this point, a heater, or thermal source, in the associated appliance, is actuated to maintain the detection chamber at a predetermined temperature for the isothermal amplification. After a predetermined time for the isothermal reaction to run, or after it runs to completion, a measurement is made with a detection station of the appliance. Reaction times may vary widely depending on the bioassay employed. For conventional isothermal bioassays, such as LAMP, predetermined times from a reaction to run is in the range of from 5 to 30 min, or in the range of from 10 to 30 min. In some embodiments, signals of a bioassay may be collected over a period of from 0 to 30 min, or a period from 2 to 30 min. When an isothermal amplification assay releases fluorescent molecules, for example, in proportion to the amount of biomolecule of interest in the reaction mixture, then a detection station may comprise an excitation beam, e.g. a laser diode of an appropriate frequency, and a fluorometer (as for example illustrated in FIG. 1B), and the readout of the assay may be a fluorescence intensity.

Figure 2F:
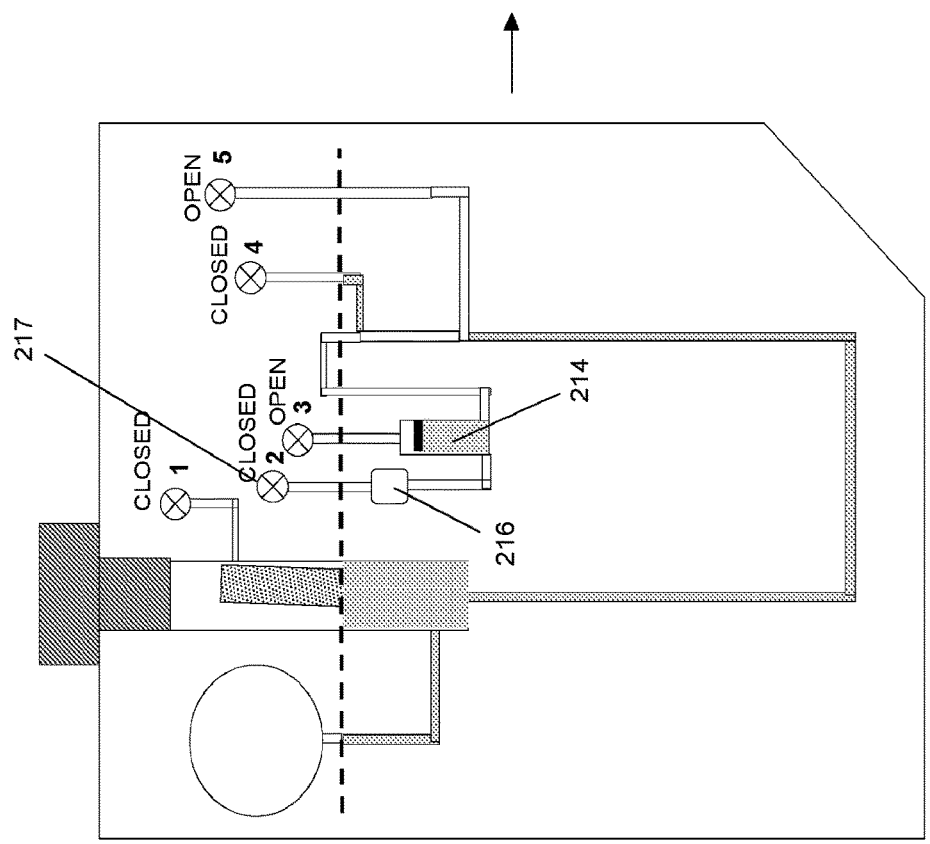

FIGS. 2A-2I illustrate the operation of an embodiment of the invention for performing an isothermal amplification and detection of a target nucleic acid wherein cartridge (200) comprises components, e.g. a lysis chamber, for sample preparation. In FIG. 2A, cartridge (200) comprises body (202) with lysis buffer chamber (or lysis reservoir) (204), sample chamber (206) with cap (221) and vent port 1 (207) and containing sample swab (219), first conduit (208), metering chamber (210) with vent port 4 (211), reagent chamber (212) with vent port 5 (213), mixing chamber (214) with vent port 3 (215), and detection chamber (216) with vent port 2 (217). In some embodiments, sample chamber (206) may also comprise a filter at its bottom outlet to prevent particulate matter from entering first conduit (208) and other passages where they may cause obstructions. Lysis buffer chamber (204) may be a conventional blister pouch (or fitted to contain a conventional blister pouch) that is design to puncture and release its fluid contents through passage (228) whenever pressed by actuator (152, FIG. 1B). Blister pouches that may be used with the invention are disclosed in Smith et al, Microfluidics and Nanofluidics, 20: 163 (2016); Smith et al, Proc. SPIE, 9705: 97050F (2016); Bau et al, U.S. patent publication 2010/0035349; and like references, which are hereby incorporated by reference. Prior to release of the lysis buffer, vent ports 1-5 (207, 217, 215, 211, and 213, respectively) are configured as follows (wherein "closed" means no liquid and no air passes through the vent port, and "open" mean no liquid but air may pass through the vent port):

| Starting Vent Port Configuration | |
| --- | --- |
| Vent Port No. | Open/Closed |
| 1 | OPEN |
| 2 | CLOSED |
| 3 | CLOSED |
| 4 | CLOSED |
| 5 | CLOSED |

This configuration allows lysis buffer (illustrated by gray shading) to move by the force of gravity through passage (228) into sample chamber (206), where it reaches a first equilibrium level (230) under gravity and where it contacts sample (219) for an incubation period. During the incubation period heat may also be applied to sample chamber (206) to help release the biomolecules of interest. After the predetermined incubation period, the valve states are changed to the following configuration:

| Second Vent Port Configuration | |
| --- | --- |
| Vent Port No. | Open/Closed |
| 1 | OPEN |
| 2 | CLOSED |
| 3 | CLOSED |
| 4 | OPEN |
| 5 | CLOSED |

In this and other embodiments, a predetermined incubation period depends on the nature of the sample and lysis reagents used. Usually, a predetermined incubation period or time is in the range of from 1 min to 30 min, or in the range of from 2 min to 15 min. The above configuration allows lysis buffer (illustrated by gray shading) to move by the force of gravity (235) from sample chamber (206) through first conduit (208), through metering chamber (210) and towards (232) open vent port (211). Lysis buffer does not move towards vent ports 2 (217), vent port 3 (215) or vent port 5 (213) because each of these are closed or in the case of vent port 5 (213), passage (233) is obstructed by bioassay reagents in reagent chamber (212). As illustrated in this figure, reagent chamber (212) is formed by disposing wax barriers (291a and 291b) up stream and downstream of the assay reagent in passage (292). In some embodiments, the passage (233) may be blocked with a low-melting point wax or hydrogel. Also, in some embodiments, one or more, or all, bioassay reagents may be stored in a blister pouch that releases the bioassay reagents by mechanical actuation, similarly to the lysis buffer. After the lysis buffer is released as illustrated it reaches a second predetermined equilibrium level (231) that is above the top outlet of metering chamber (210). The amount of lysis buffer, the sizes and the positions in body (202) of sample chamber (206) and metering chamber (210) are selected so that the predetermined equilibrium level (231) is above the top outlet of metering chamber (210).

In some embodiments, vent port 4 (211) may be operationally associated with a pump or pressure source, e.g. pump 1, of the appliance so that pressure is applied to the column of lysis buffer in metering chamber (210) and first conduit (208) to force it back into sample chamber (206) to provide mixing and incubation of lysis buffer with biological sample on swab (219). Vent port 4 (213) is operationally associated with pump 1 (154, FIG. 1B) which generates pressure at vent port 4, e.g. by moving a piston in pump 2 a predetermined amount, upon receiving an actuation signal from control system (162, FIG. 1B). In one embodiment, pumps 1 and 2 may be precision piston-style pumps, e.g. Idex Health & Science (Lake Forest, IL); Pen-Pump (Takasago Fluidics Systems, Westborough, MA); or the like. Other types of pumps, e.g. diaphragm, and other pressure sources may be employed with the inventions.

After such application of pressure from vent port 4 (211), the lysis buffer returns to predetermined equilibrium level (231), as illustrated in FIGS. 2B and 2C, and the vent port configuration is changed as follows:

Third Vent Port Configuration

| Vent Port No. | Open/Closed |
| --- | --- |
| 1 | CLOSED |
| 2 | CLOSED |
| 3 | OPEN |
| 4 | CLOSED |
| 5 | OPEN |

Figure 2E:
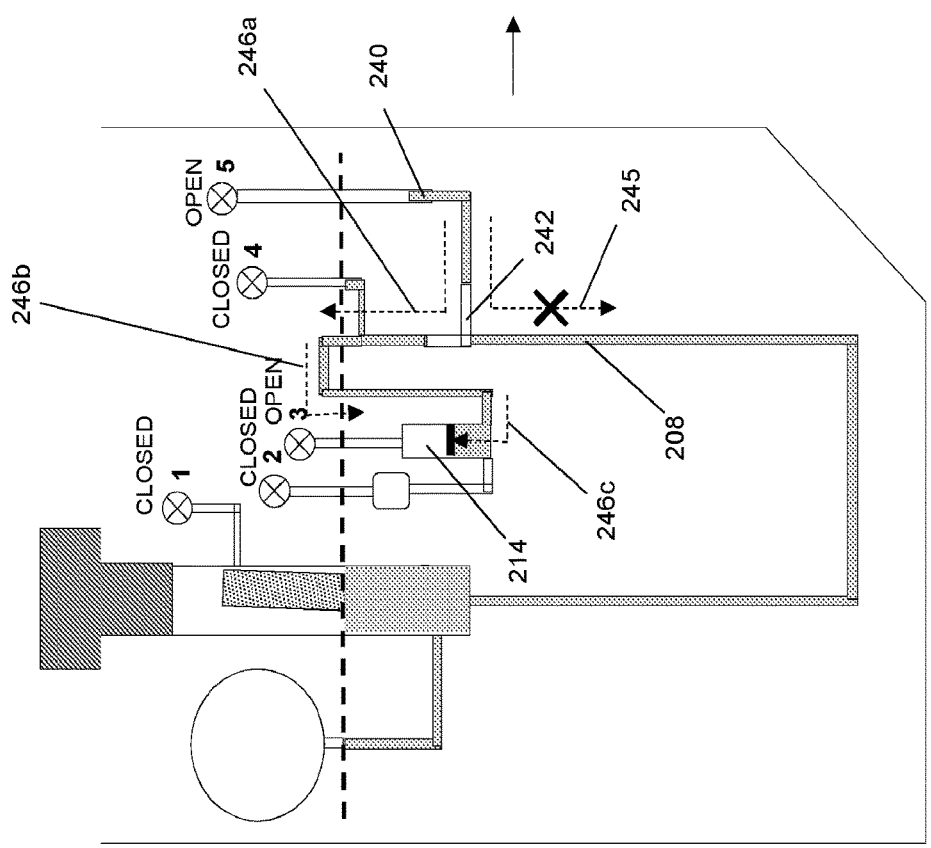

As illustrated in FIG. 2E, in this configuration pressure is applied through vent port 5 (213) to force bioassay reagents in reagent chamber (212) to flow through passages indicated by arrows (246a, 246b and 246c) and into mixing chamber (214). Vent port 5 (213) is operationally associated with pump 2 (156, FIG. 1B) which generates pressure at vent port 5 upon receiving an actuation signal from control system (162, FIG. 1B), e.g. by moving a piston in pump 2 a predetermined amount. Bioassay reagent (240) does not flow through first conduit (208) as indicated by arrow (245) because first conduit is designed (by selecting length, cross-section, degree of crenulation, and like parameters) to present fluid resistance to such flow. In some embodiments, first conduit (208) is designed to have a zig-zag pattern and a length which is sufficient to block any substantial flow of bioassay reagent into first conduit (208). The step of forcing bioassay reagent (240) and the metered amount of lysis buffer into mixing chamber (214) allows any bubbles (242) in the line to be removed before transferring the mixture to a temperature cycling chamber or directly to detection chamber (216). FIG. 2F illustrates the distribution of lysis buffer and reaction mixture in cartridge (100) after the bioassay reagents and metered sample have been forced into mixing chamber (214).

Although the cartridge of FIGS. 2A-2I show the bioassay reagent being held in a single reagent chamber (212) directly connected to first conduit (208) and metering chamber (210), in some embodiments, there may be multiple reagent chambers that hold different components for a bioassay, for example, primers in one compartment and polymerase in another compartment. Such compartments may be arranged in serial fashion, so that the components are stored separately, but that an application of pressure forces all components to flow through the same passage to mixing chamber (214) for mixing. Alternatively, multiple components can each be stored separately in parallel branches each with a single reagent chamber connected at one end to first conduit (208) and metering chamber (210) and connected at the other end a vent port operationally associated with a pump or other pressure source. In the latter, embodiment, bioassay reagents may be delivered independently to mixing chamber (214) or to a temperature cycling chamber or detection chamber (216). In both alternatives, bioassay reagents may be further isolated by sealing inlet and outlet passages with a wax, hydrogel, or like obstruction, that can be removed by heating from an appliance.

Returning to FIG. 2F, after step 5 (that is, after lysis buffer, biomolecules of interest, and bioassay reagents are mixed to form a reaction mixture in mixing chamber (214)), the vent configuration is changed to permit reaction mixture in mixing chamber (214) to be pulled into detection chamber (216) by applying vacuum to vent port 2 (217). There are several alternative vent port configurations which will allow such transfer. Namely, vent port 2 (217) is open and any one or all of the vent ports 1, 3, 4 and/or 5 may be open. In some embodiments, the following vent port configuration is employed in step 5:

Fourth Vent Port Configuration (1st alternative)

| Vent Port No. | Open/Closed |
| --- | --- |
| 1 | CLOSED |
| 2 | OPEN |
| 3 | OPEN |
| 4 | CLOSED |
| 5 | CLOSED |

In some embodiments, the following alternative vent port configuration may be employed:

Fourth Vent Port Configuration (2nd alternative)

| Vent Port No. | Open/Closed |
| --- | --- |
| 1 | OPEN |
| 2 | OPEN |
| 3 | CLOSED |

-continued

Fourth Vent Port Configuration (2$^{nd}$ alternative)

| Vent Port No. | Open/Closed |
|---|---|
| 4 | CLOSED |
| 5 | CLOSED |

Figure 2H:
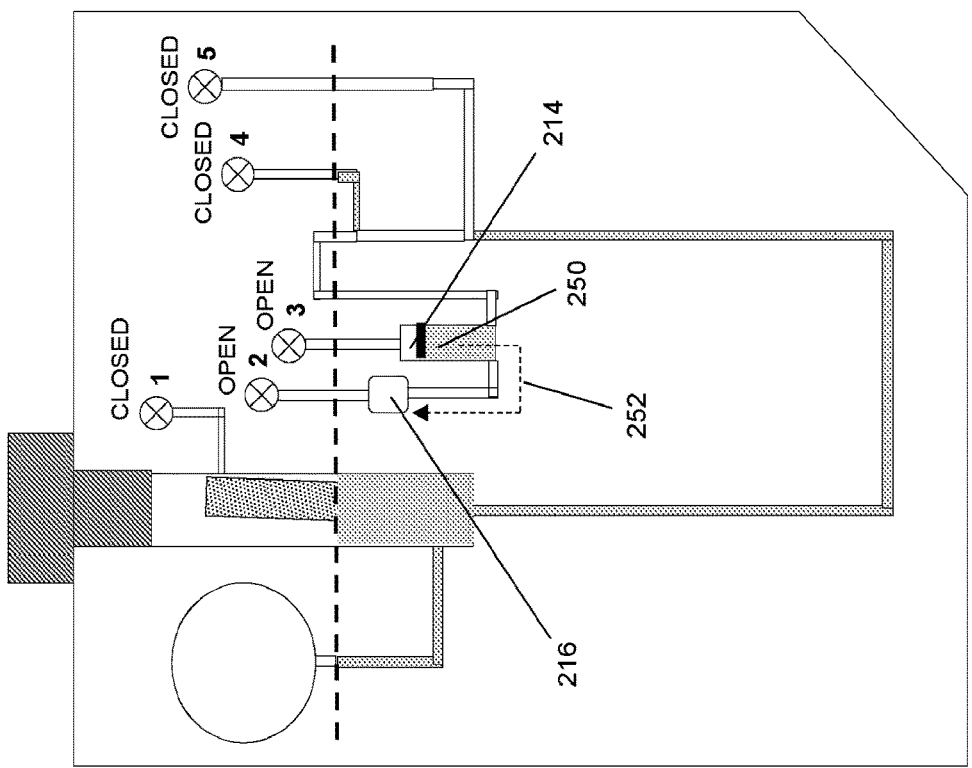
Figure 2G:
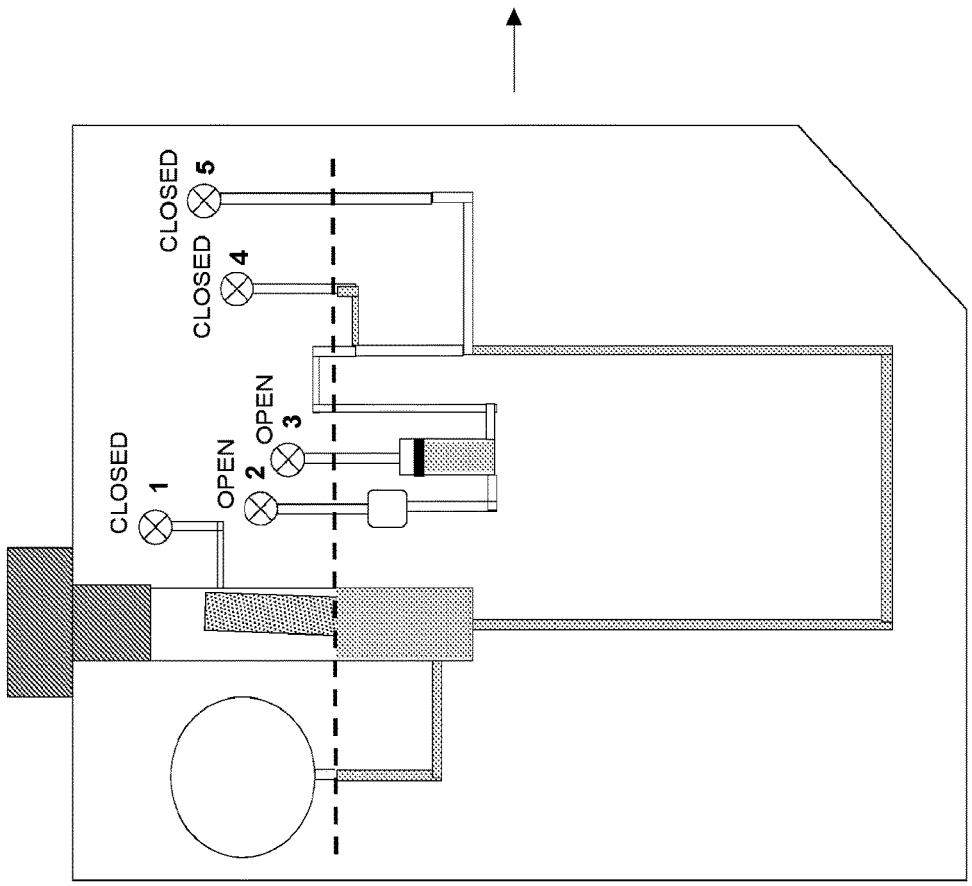
Figure 2I:
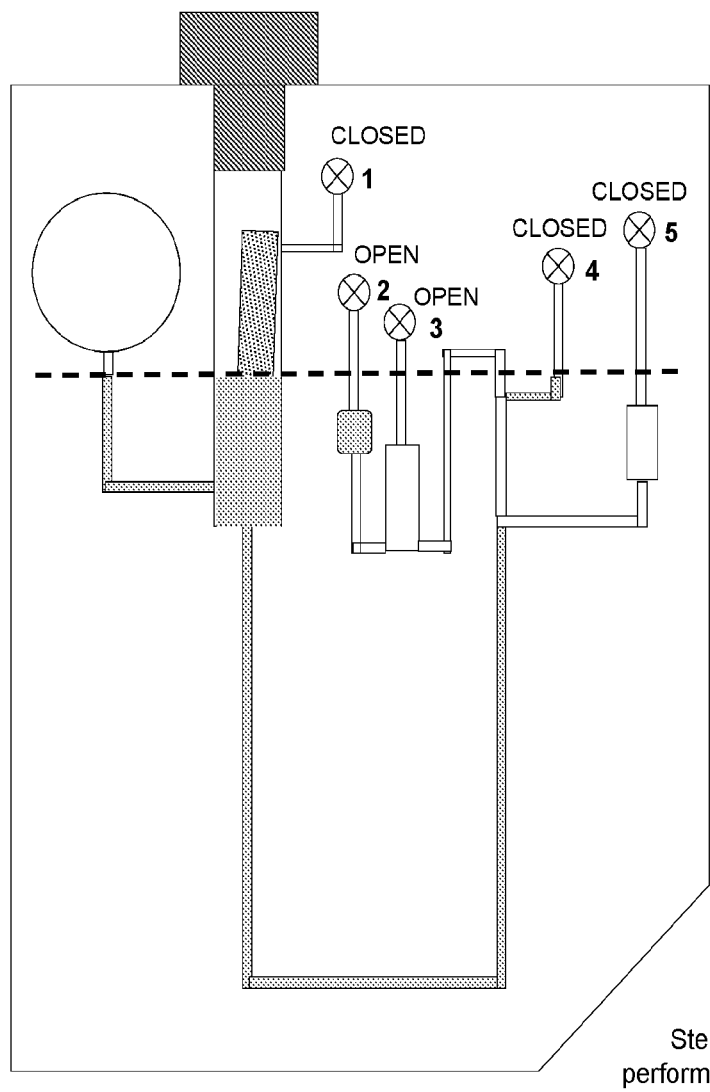

As illustrated in FIG. 2H, employing the first alternative vent port configuration, upon application of vacuum to vent port 2, reaction mixture (250) is pulled from mixing chamber (214) into detection chamber (216), as indicated by arrow (252), to give the final distribution of lysis buffer and reaction mixture (250) as shown in FIG. 2I. Whenever the biomolecule of interest is a polynucleotide and its detection is based on an isothermal reaction, in the illustrated embodiment, no further movement of liquid is necessary. At this point, a heater, or thermal source, in the associated appliance, is actuated to maintain the detection chamber at a predetermined temperature for the isothermal amplification. After a predetermined time for the isothermal reaction to run, or after it runs to completion, a measurement is made with a detection station of the appliance. Reaction times may vary widely depending on the bioassay employed. For conventional isothermal bioassays, such as LAMP, predetermined times from a reaction to run is in the range of from 5 to 30 min, or in the range of from 10 to 30 min. In some embodiments, signals of a bioassay may be collected over a period of from 0 to 30 min, or a period from 2 to 30 min. When an isothermal amplification assay releases fluorescent molecules, for example, in proportion to the amount of biomolecule of interest in the reaction mixture, then a detection station may comprise an excitation beam, e.g. a laser diode of an appropriate frequency, and a fluorometer (as for example illustrated in FIG. 1B), and the readout of the assay may be a fluorescence intensity.

Figure 2J:
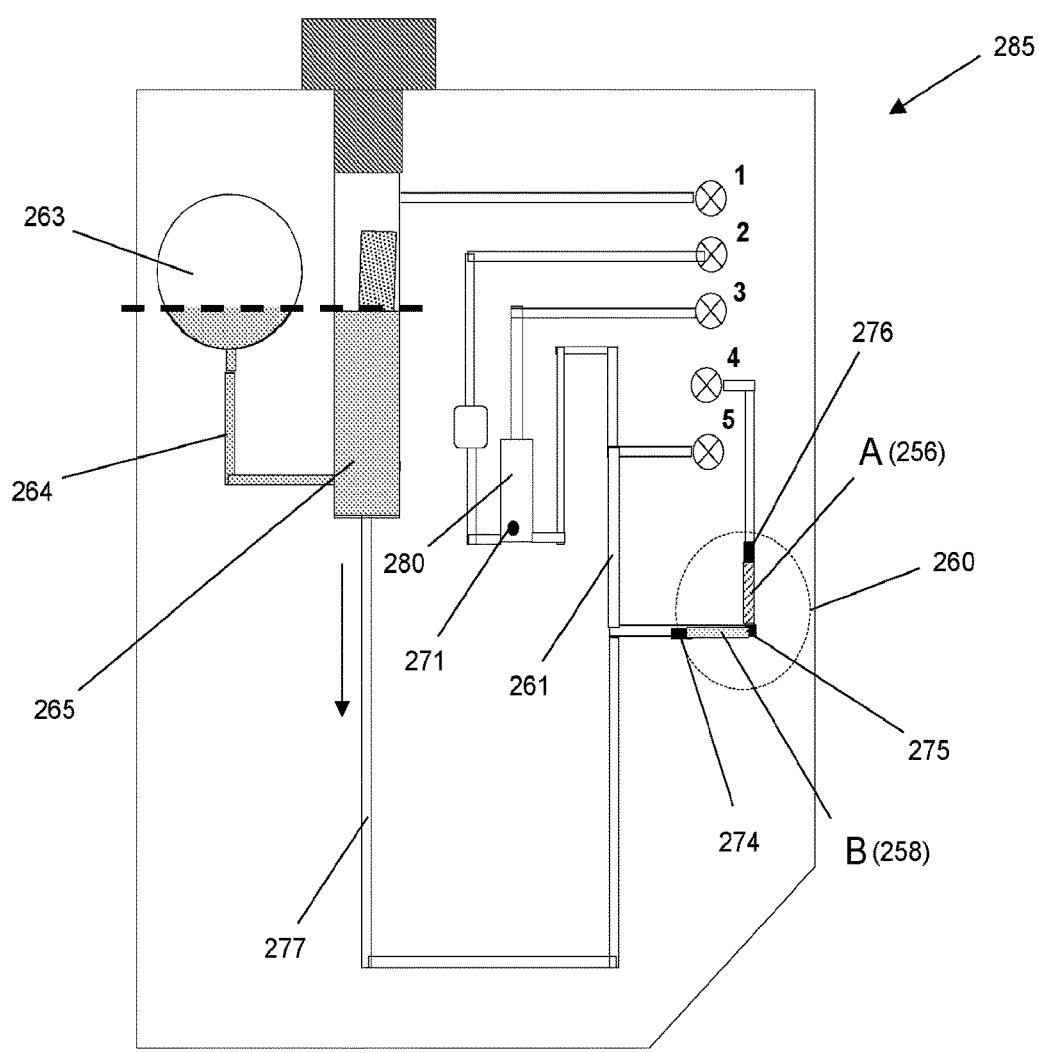
FIGS. 2J-2N illustrate the operation of an embodiment employing bubble-suppressing wax.
Figure 2K:
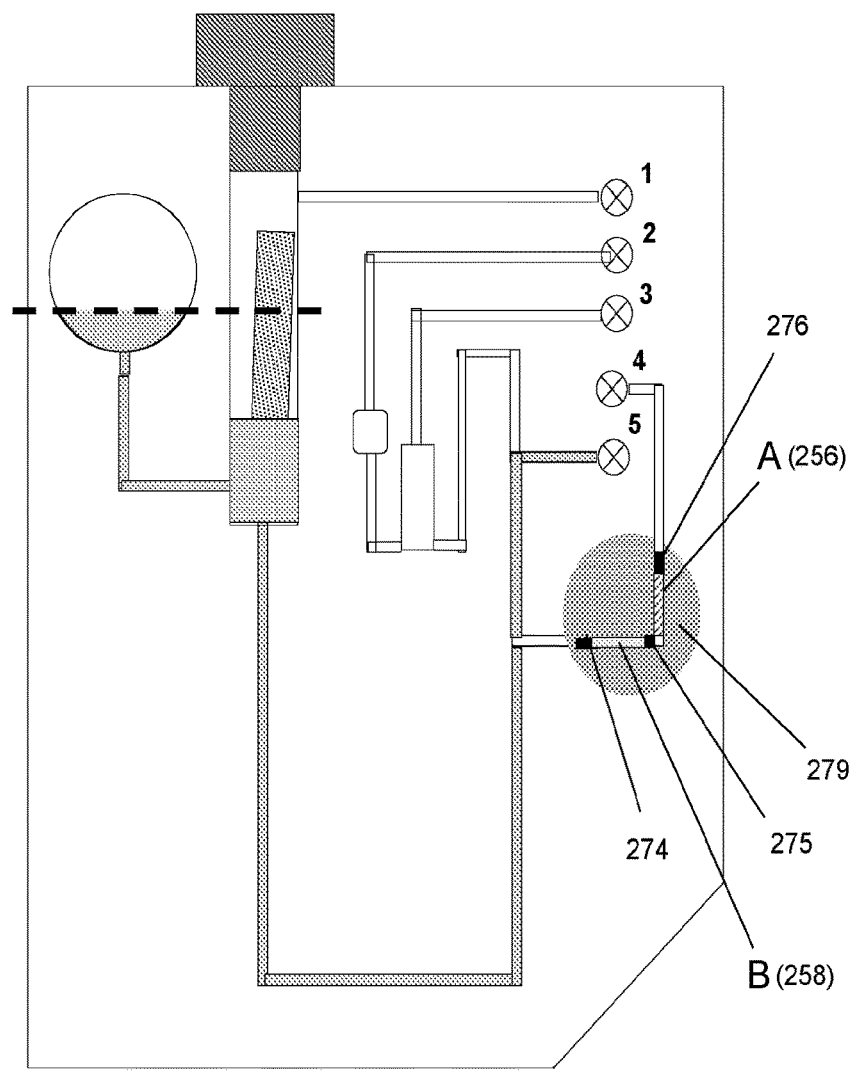
Figure 2L:
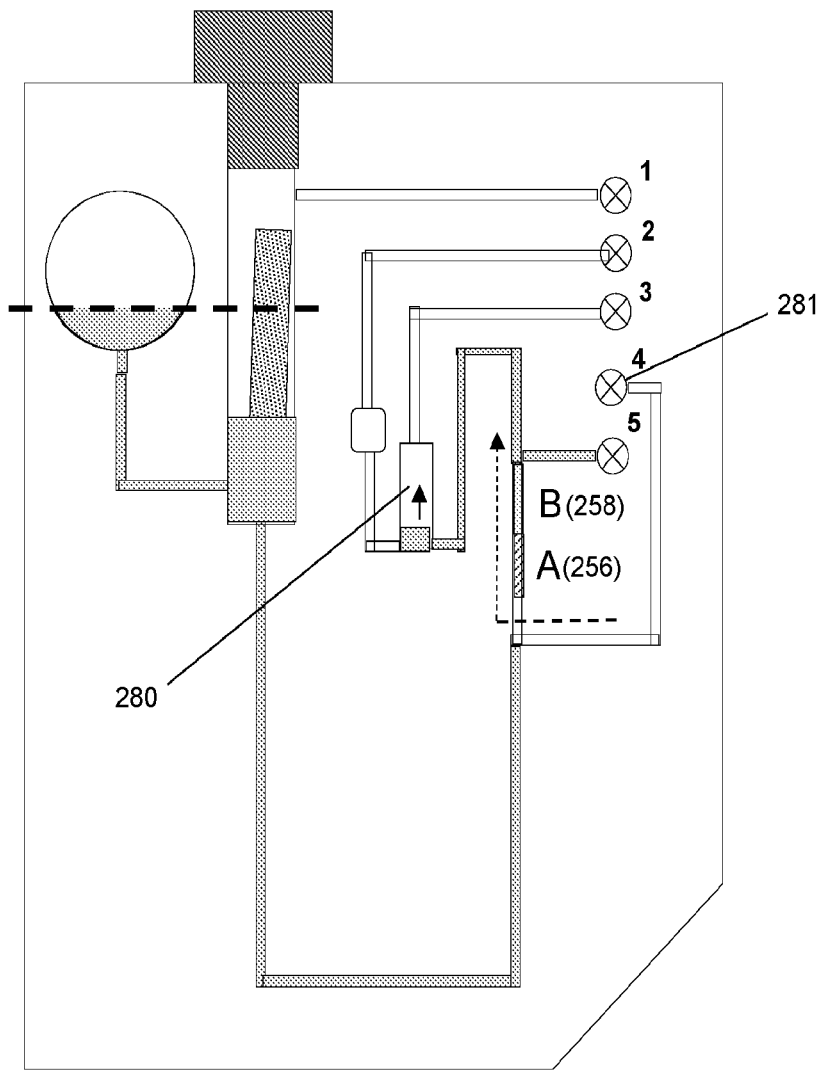
Figure 2M:
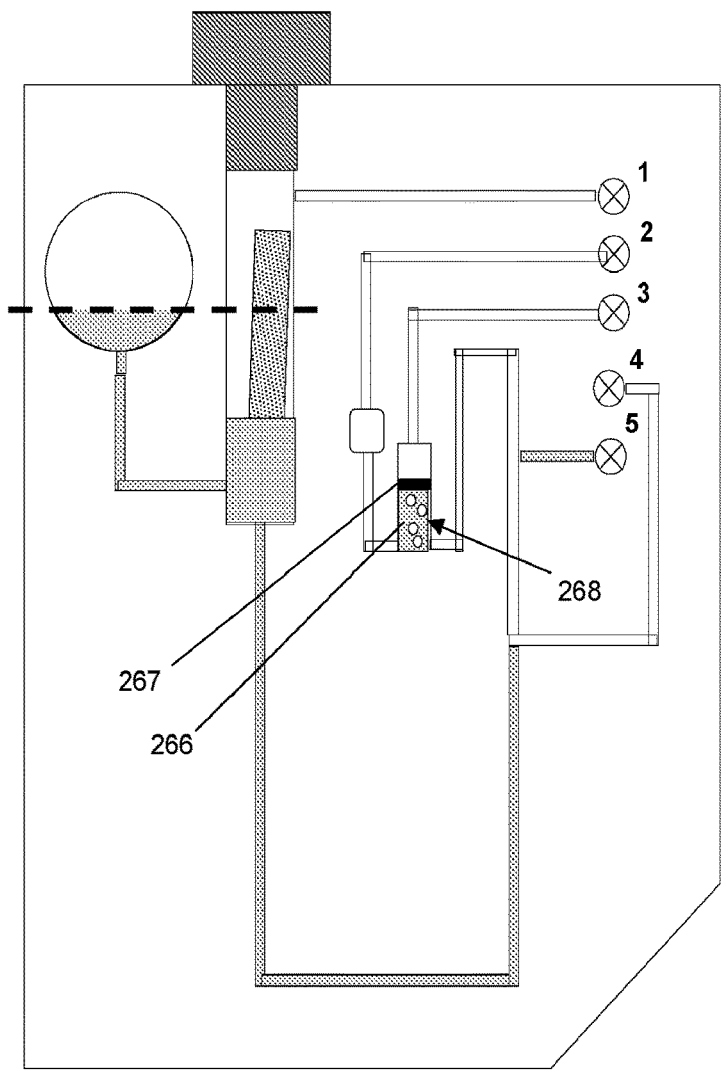
Figure 2N:
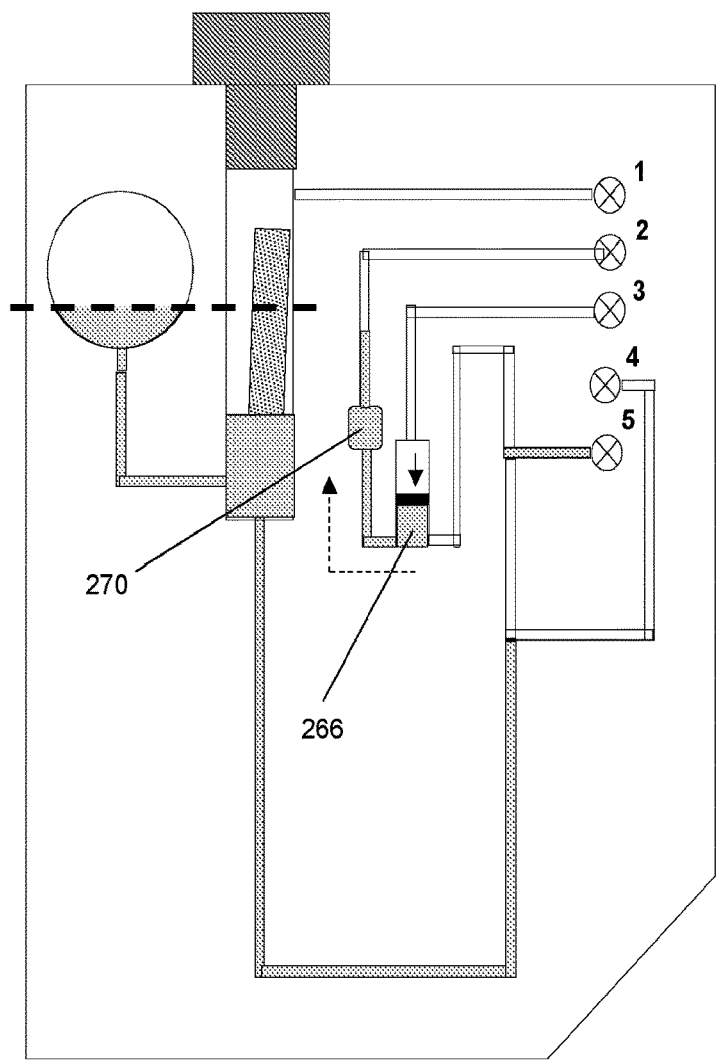

FIGS. 2J-2N illustrate an embodiment that does not employ gravity to fill the metering chamber. Such embodiments are advantageous in that the relative placement of the metering chamber and the sample chamber is less constrained and the movement of fluids is faster when solely driven by pressure and/or vacuum. An exemplary embodiment is illustrated by cartridge (285) of FIG. 2J. Reagent chamber (260) consists of two reagents A (256) and B (258) separated and isolated by wax barriers (274, 275 and 276). Sample chamber (265) is shown with lysis buffer released from lysis chamber (263) through passage (264). Vent ports 1-5 are configured as shown on the table of FIG. 2J so that lysis buffer containing biomolecule of interest can be forced into metering chamber (261) through first conduit (277), as shown in FIG. 2K. Next wax barriers (274, 275 and 276) are melted by heating reaction chamber (260) with heating element (279) which is located in the appliance (not shown). The vent port configuration is changed as shown in the table of FIG. 2L and the liquefied wax and reagents A (256) and B (258) are driven into mixing chamber (280) by air pressure from vent port 4 (281). As shown in FIG. 2M, reaction mixture (266) (consisting of assay reagents A and B and lysis buffer with released biomolecules) is covered with layer (267) of liquid wax as air (268) continues to be pumped into mixing chamber (267) to thoroughly mix the assay reactants and analyte. Vent port configuration is changed to that as shown in the table of FIG. 2N, so that after a predetermined mixing time, reaction mixture (266) is forced into detection chamber (270). Optionally, as illustrated in FIG. 2J, a predetermined amount of wax (271) may also be disposed directly in mixing chamber (267) to ensure sufficient wax to effectively suppress bubble formation. Also optionally, an additional heating element may be provided for heating mixing chamber (280) during the mixing step to maintain the wax in a liquid state.

Figure 3A:
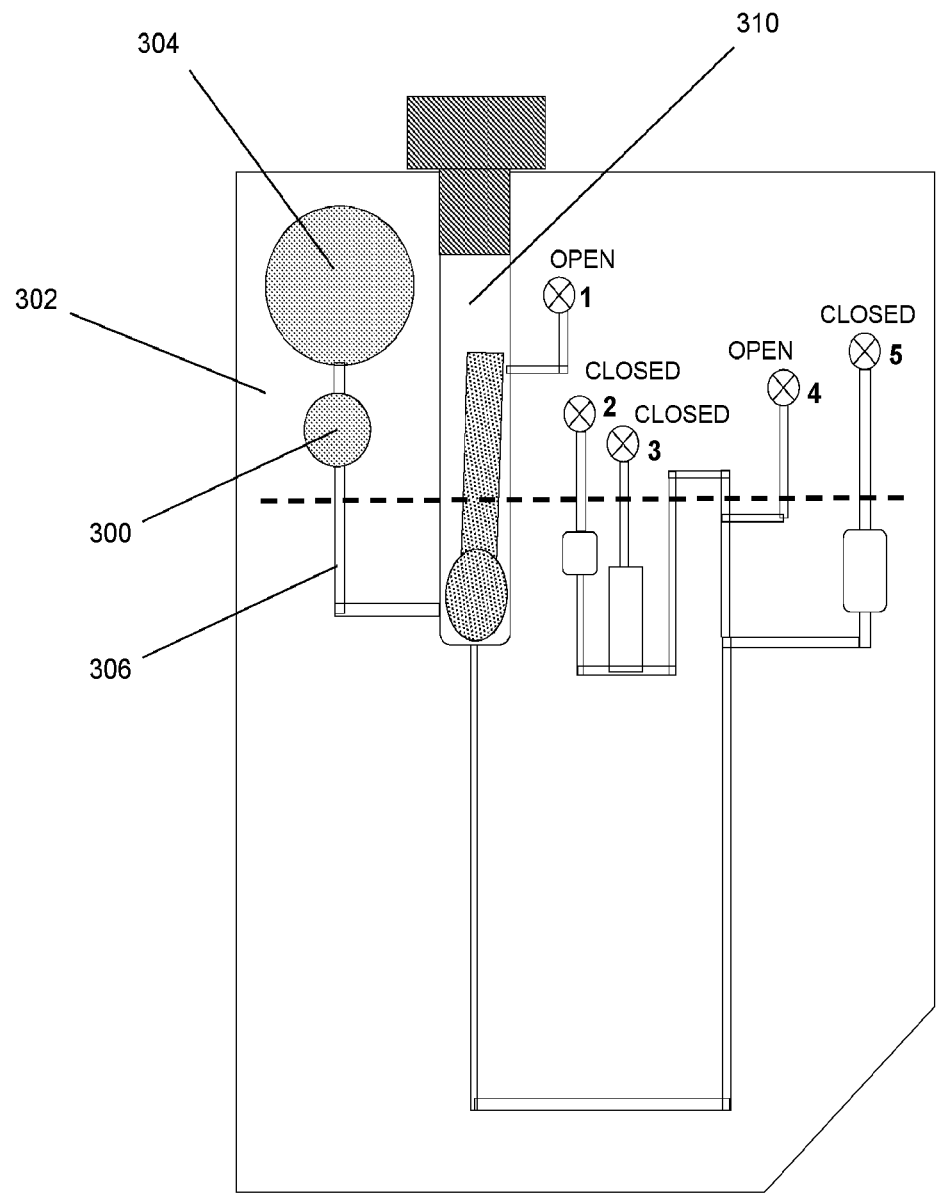
FIG. 3A illustrates a cartridge embodiment that includes a chamber for nuclease inhibitors.
Figure 3B:
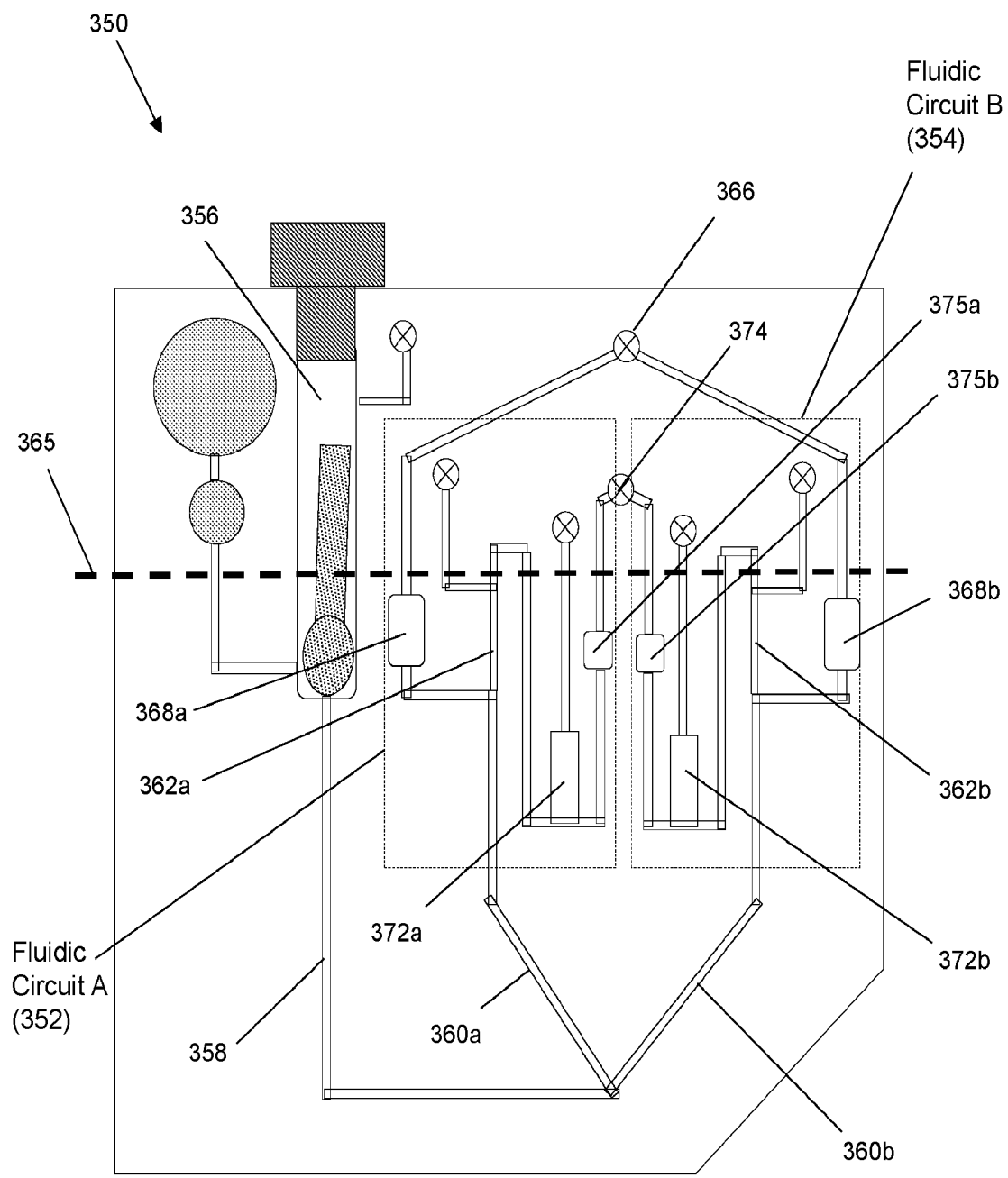
FIG. 3B illustrates a cartridge embodiment that include two reagent chambers, two metering chambers, two mixing chambers and two detection chambers for performing two bioassays with isothermal amplification of two polynucleotides from a single sample.
Figure 3C:
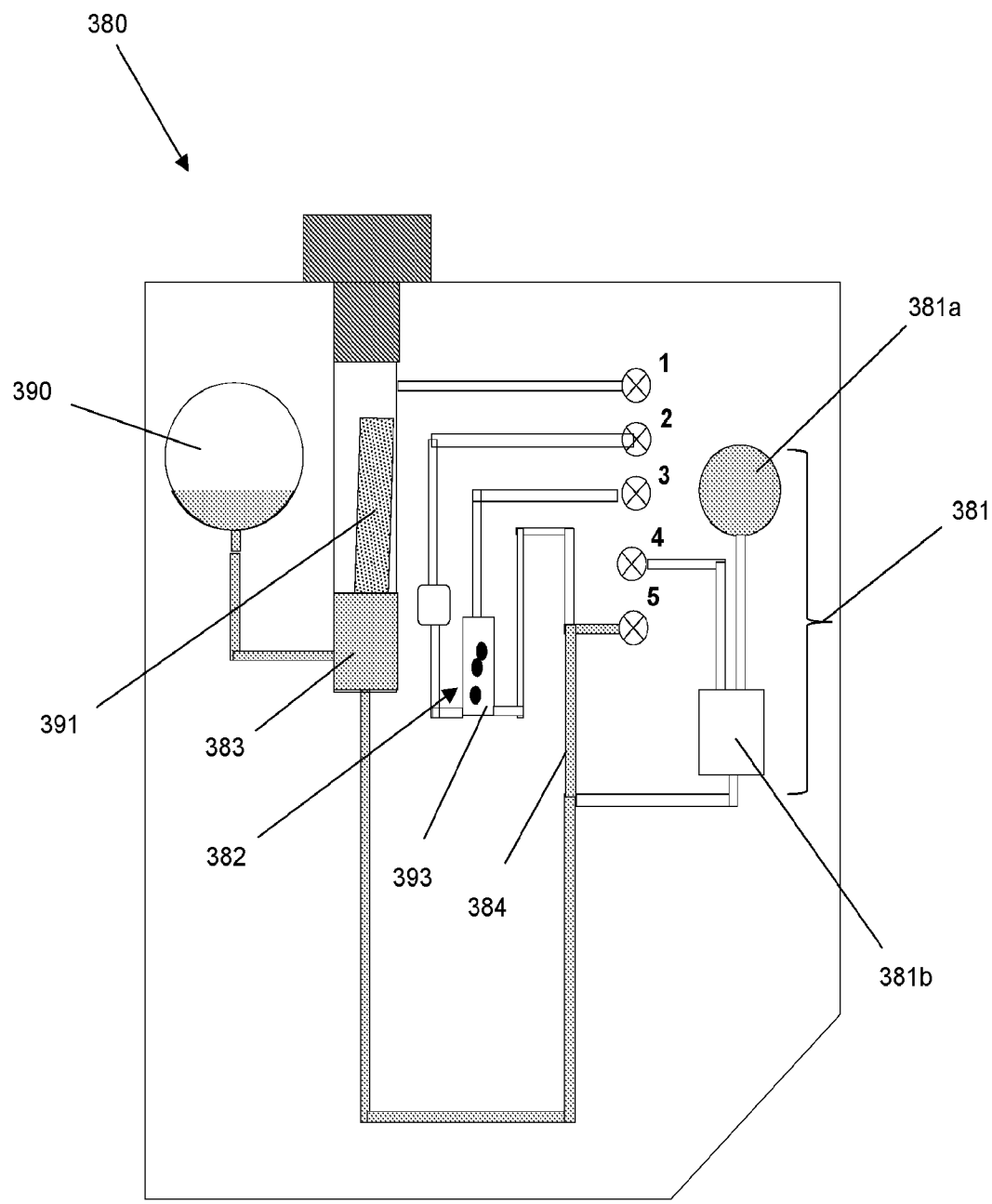
FIGS. 3C-3E illustrate a cartridge embodiment that includes a second blister pack and dried reagents disposed in the mixing chamber so that the mixing chamber performs functions (i.e., reagent storage) of the reagent chamber and mixing chamber simultaneously.
Figure 3D:
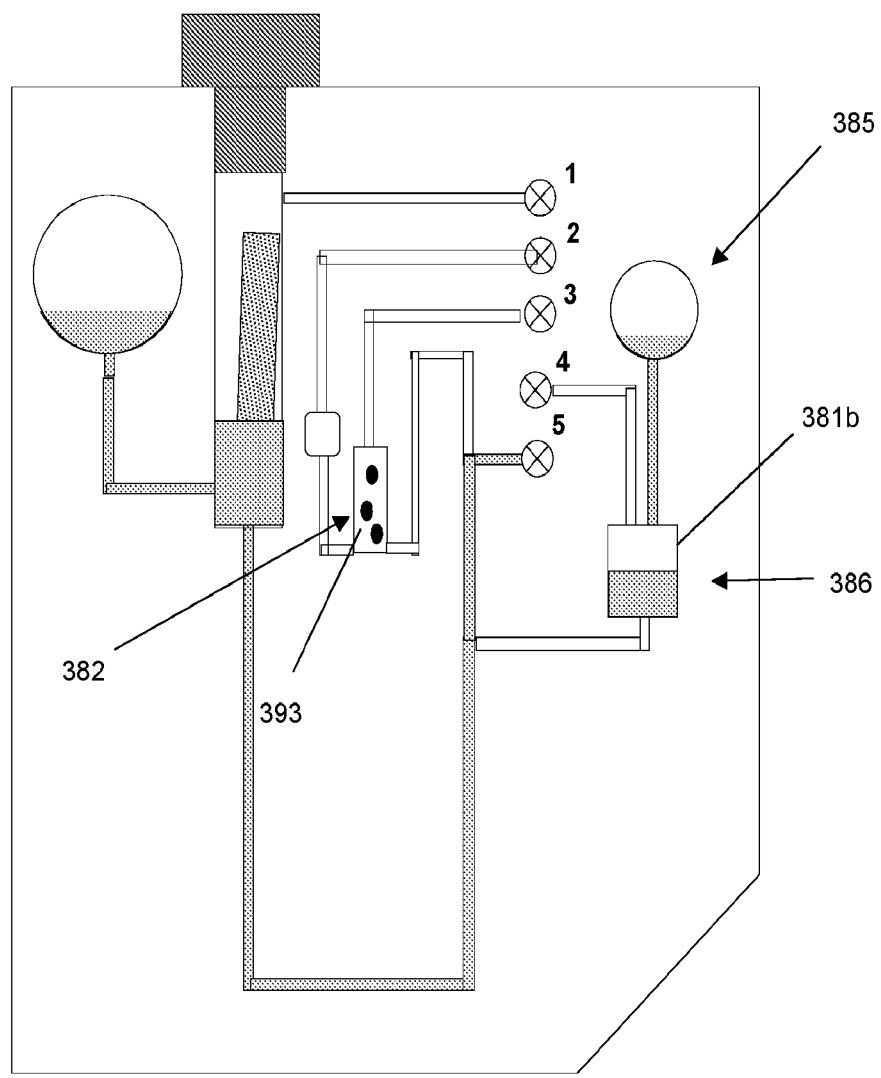
Figure 3E:
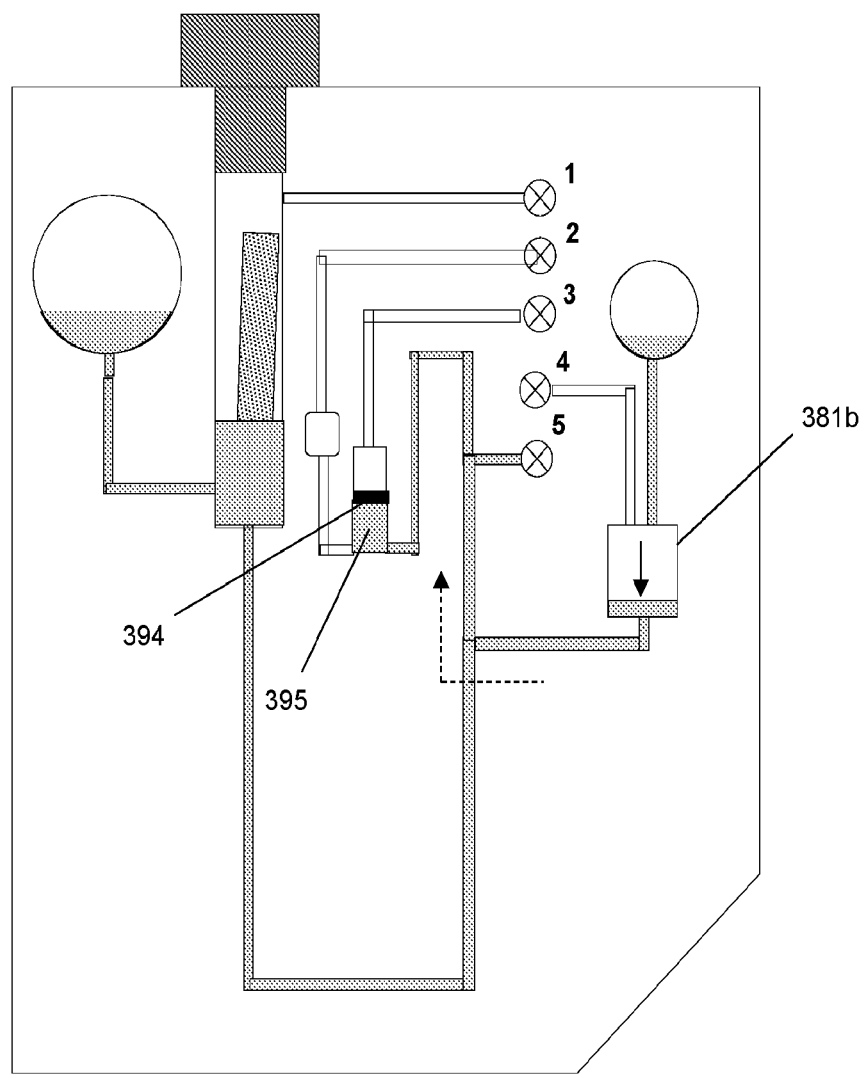

FIGS. 3C-3E illustrate the design and operation of an embodiment having a reagent chamber comprising a blister pack and a mixing chamber comprising dried reagents. Cartridge (380) has components similar to those of the cartridge of FIG. 2J, except that mixing chamber (393) contains dried reagents (382) and reagent chamber (381) comprises blister pack (381a) and holding chamber (381b), the latter of which is connected at its top to vent port 4 and to blister pack (381a). In this example, three different dried reagents are illustrated for an isothermal amplification reaction: primers and nucleoside triphosphates, polymerase, and a predetermined quantity of wax. Holding chamber (381b) is connected at its bottom to the bottom of metering chamber (384). Cartridge (380) is shown at a stage wherein a sample (391) has incubated in lysis buffer (383) released by blister pack (390) and the lysis buffer containing released polynucleotides has been moved into and through metering chamber (384) to vent port 5. After these operations have occurred, as illustrated in FIG. 3D, blister pack (381a) containing a reaction buffer is punctured and the reaction buffer is released into holding chamber (381b). Upon reaching the mixing chamber (393) the reaction buffer will re-hydrate dried reagents (382) upon heating and mixing. After release of reaction buffer into holding chamber (381b), vent ports are configured as shown in the table below to permit movement of the reaction buffer into mixing chamber (393) by pressure exerted from vent port 4. As shown in FIG. 3E, the reaction buffer hydrates the dried reagents to form a reaction mixture through which air (or other gas) under pressure from vent port 4 is injected to insure full hydration and mixing of the assay reagents and polynucleotides from the sample. As shown in FIG. 3E, the liquid wax forms a bubble suppressing layer (394) over reaction mixture (395). In some embodiments, a portion of a predetermined quantity of wax may be disposed in holding chamber (381b).

| Port | Open/Closed |
|---|---|
| 1 | Closed |
| 2 | Closed |
| 3 | Open (vent) |
| 4 | Open (pressure) |
| 5 | Closed |

Figure 3F:
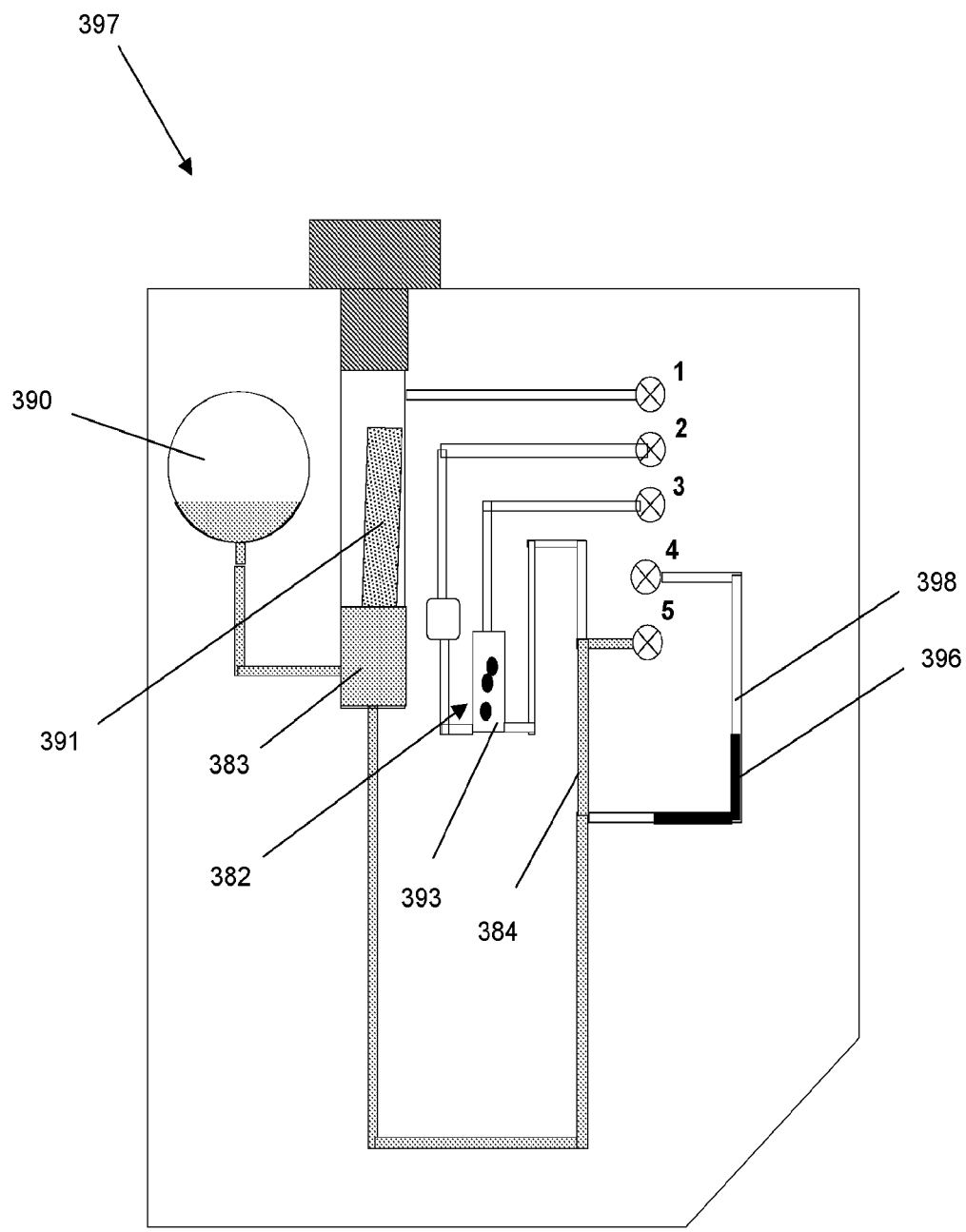
FIG. 3F illustrates a cartridge embodiment whose reagent chamber contains only a wax.

FIG. 3F illustrates another embodiment (397) of a cartridge of the invention. This embodiment is similar to the embodiment of FIG. 3C except that it does not include reagent chamber (381) comprising blister pouch (381a) and holding chamber (381b). Instead, passage (398) serves as a reagent chamber storing only wax (396) (which as above may be the only wax in cartridge (397) or may be a portion of the wax employed while the remainder may be stored in mixing chamber (393)). In operation, a bioassay may be performed in cartridge (397) similarly to the steps illustrated for cartridge (285) in FIGS. 2J-2M. Namely, wax (396) is melted, after which pressure from vent port 4 pushes wax (396) through metering chamber (384) so that a metered volume of lysis buffer, in turn, is pushed into mixing chamber (393). Depending on the location of wax (396) in passage (398), either wax (396) or air may be in direct contact with the metered volume of metering chamber (384). In this embodiment, however, fluid for reconstituting dried reagents (382) are incorporated into lysis buffer (383) and delivered to mixing chamber (393) after the metered volume is forced into mixing chamber (393).

In some embodiments, for example, where target biomolecules are nucleic acids, such as RNA or DNA, lysis buffers may include additional components to protect target RNAs or DNAs from degradation after extraction by the lysis buffer. In particular, a lysis buffer may contain or be mixed with nuclease inhibitors that are designed to inactivate nucleases that may be release along with target RNAs or DNAs by a lysis buffer. FIG. 3A illustrates a cartridge embodiment that includes inhibitor chambers (300) positioned in cartridge body (302) downstream of lysis buffer chamber (304) along passage (306) that connects both chambers to sample chamber (310). Nuclease inhibitors may have a variety of compositions, e.g. antibodies, organic polymers, and the like, Raines et al, U.S. patent publication 2013/0344563; Latham et al, U.S. Pat. No. 7,264,932; which are incorporated by reference. In some embodiments, lysis buffer and nuclease inhibitors are stored separately, such that a lysis buffer when released (e.g. by puncturing a blister pouch), in turn, releases the nuclease inhibitor from its storage chamber as it flows to the sample chamber. The nature of the nuclease inhibitor employed is a factor in how it is stored in a cartridge. In some embodiments, nuclease inhibitors may be stored in a porous material that a lysis buffer flows through after puncturing a blister pouch, as illustrated in FIG. 3A. In this manner, as the lysis buffer releases target RNAs or DNAs from the sample, nuclease inhibitors will be present to prevent degradation of the target RNAs or DNAs. An exemplary porous material for storing a nuclease inhibitor is porous material is a polyethersulfone (PES) frit, e.g. available from Porex Corporation.

As mentioned above, cartridges of the invention may be used with a variety of assays for biomolecules, including polymerase chain reactions (PCRs), although such applications may require additional chambers and corresponding modifications to an appliance which are within the scope of abilities of those of ordinary skill in the art.

In some embodiments, it may be desirable to measure the presence of at least two polynucleotides, for example, a target polynucleotide and a control, or internal standard, polynucleotide. The latter polynucleotide may be internal, or indigenous, to the sample or it may be an external, or exogenous, molecule that is added to the sample in a predetermined quantity. For example, an internal standard polynucleotide may be pre-loaded into the sample chamber as a dried reagent that is re-hydrated upon exposure to the lysis buffer. Alternatively, such an internal standard polynucleotide may be included with the bioassay reagents. Or, as another alternative for bioassays with polynucleotide amplification, an additional set of primers may be included with the assay reagents for amplifying an internal standard indigenous to the sample. In some embodiments, by a relative signal generated by the internal standard and an analyte polynucleotide, a quantity of analyte polynucleotide may be estimated. One of ordinary skill would understand that a plurality of fluidics circuits of the invention (for example, comprising interconnected metering chamber, reagent chamber, mixing chamber and detection chamber, including various vent ports) can be constructed or formed within a single cartridge and that a single sample can be split into a plurality of portions (of the same or different amounts) for separately analyzing a plurality of different analytes from the same sample.

As illustrated in FIG. 3B, two sets of chambers and passages (i.e. for metering, reagent, mixing, and detection) may be fabricated in single cartridge (350) of the invention for detecting or measuring two polynucleotides of interested. Various embodiments for detecting a larger plurality of target polynucleotides may be fabricated using the same principle of operation as cartridges designed for detecting a single or two polynucleotides. Cartridge (350) works according to the same principle of operation as the cartridge of FIGS. 2A-2I, except that the mirror image of the chamber and passage arrangement of the cartridge of FIGS. 2A-2I has been inserted so that there are two fluidic circuits (352 and 354) for reagent mixing and detection. As with FIGS. 2A-2I, after the sample is inserted and the lysis buffer release, it flows under gravity into sample chamber (356) and then into first conduit (358), then into the two branches (360a and 360b) of first conduit (358), then into metering chambers (362a and 362b) of fluidic circuits (352 and 354, respectively) up to a predetermined equilibrium level (365). As with FIGS. 2A-2I, pressure is applied to vent port (366) which forces reagents of reagent chambers (368a and 368b) through metering chambers (362a and 362b) and into mixing chambers (372a and 372b). After mixing in (372a and 372b) to form a reaction mixtures for the bioassays, vacuum is applied to vent port (374) to pull the reaction mixtures into detection chambers (375a and 375b, respectively). One of ordinary skill in the art would recognize that the appliance used with the cartridge of FIG. 3C would require appropriate modifications and additions, e.g. multiple detection stations, additional vent ports, and the like, for the cartridge of FIG. 3C to operate as described for the embodiment of FIGS. 2A-2I.

Figure 5:
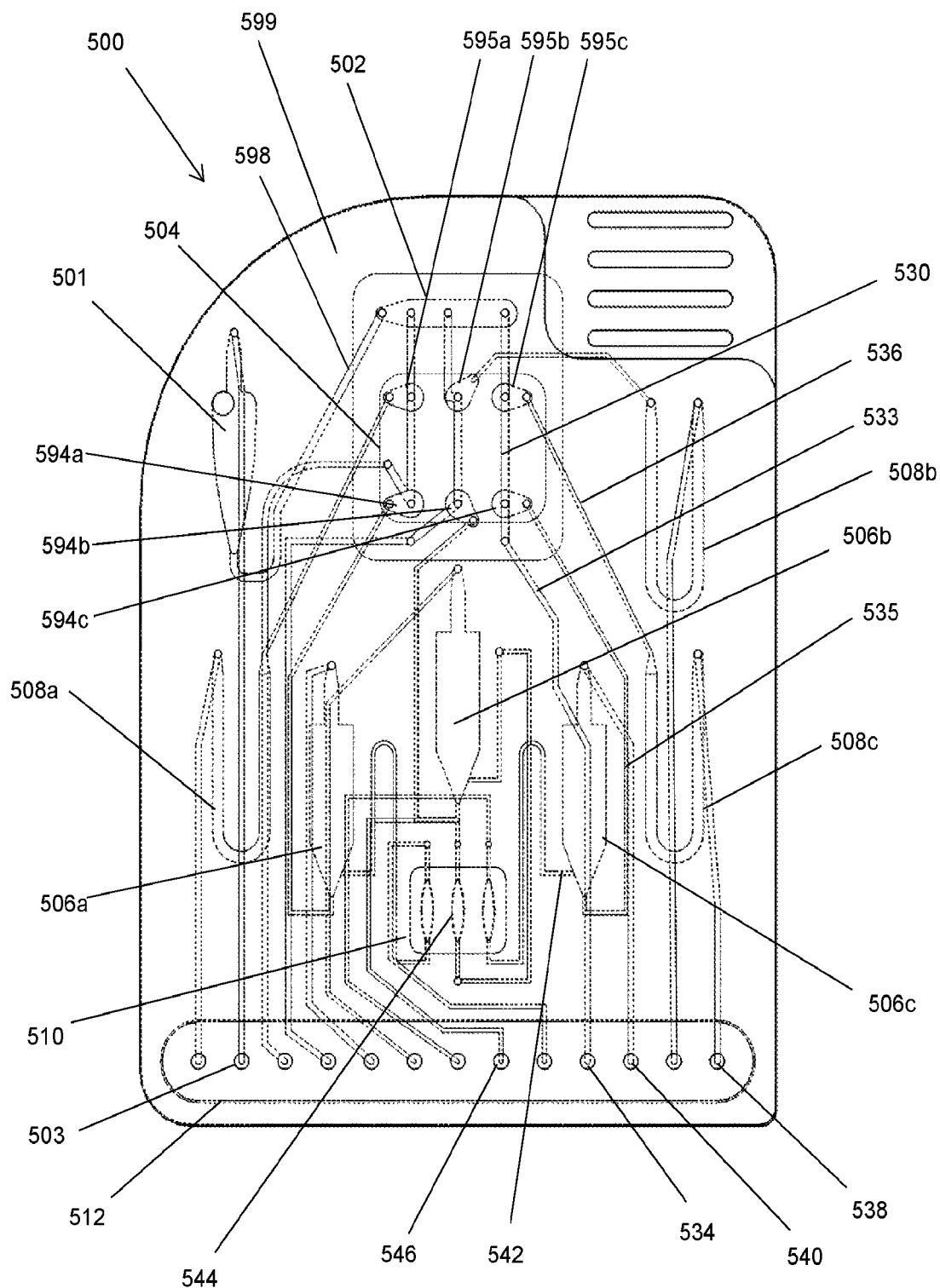
FIG. 5 illustrates a cartridge embodiment that includes three fluidics circuits for performing three bioassays with isothermal amplification of three polynucleotides (the same or different) from a single sample. Each fluidics circuit comprises a metering chamber, mixing chamber, reagent reservoir and detection chamber.

FIG. 5 illustrates a cartridge configured with three fluidics circuits for measuring three analytes, such as polynucleotides, from the same sample using an isothermal amplification and detection bioassay. Cartridge (500) has in planar body (599) in which are disposed single sample chamber (501) to which sample is added, after which it is driven by pressure supplied by vent port (503) through first conduit (598) to separation chamber (502) where the sample fluid is split into three portions (for example, using valves (595a, 595b and 595c) which portions are distributed to separate metering chambers (in dashed area 504, which in this embodiment includes valves (595a, 595b and 595c) and (594a, 594b and 594c)). Sample fluid in separate metering chambers (504) are combined with bioassay reagents from separate reagent chambers (508a, 508b and 508c) in respective mixing chambers (506a, 506b and 506c), after which resulting reaction mixtures are forced into their respective detection chambers (in area 510). In this embodiment, movement of fluid through cartridge (500) is accomplished by programmed opening, closing, and supplying pressure or vacuum through vent ports of vent port array (512) in the same manner as described for the embodiments (e.g. FIGS. 2J-2N) having a single fluidics circuit. Such operation of the fluidics circuits of cartridge (500) is exemplified by the fluidics circuit comprising metering chamber (530). In this circuit, sample fluid flows into metering chamber (530) and through overflow passage (533) because vent port (534) is open and vent port (540) is closed. Note that FIG. 5 depicts at least two layers of microfluidics features so that passage (533) passes below or above metering chamber (506c). The figure is not intended to depict passage (533) in fluid communication with metering chamber (506c). After such loading, vent port (534) is closed, vent port (540) is opened and vent port (538) is opened (and supplied with air pressure) so that the metered volume of sample fluid and reagents from reagent chamber (508c) may be pushed into mixing chamber (506c) through passages (536) (530) and (535). (In alternative embodiments, bioassay reagents and sample fluid may be driven into mixing chamber (506c) by vacuum supplied to vent port (540)). After mixing, the resulting reaction mixture is drawn through passage (542) into detection chamber (544) by applying vacuum to vent port (546). In some embodiments, passage (542) may connect with mixing chamber (506c) above the inlet of passage (535) (as shown) to avoid bubbles that may become lodged in the inlet during the mixing process.

Figure 6:
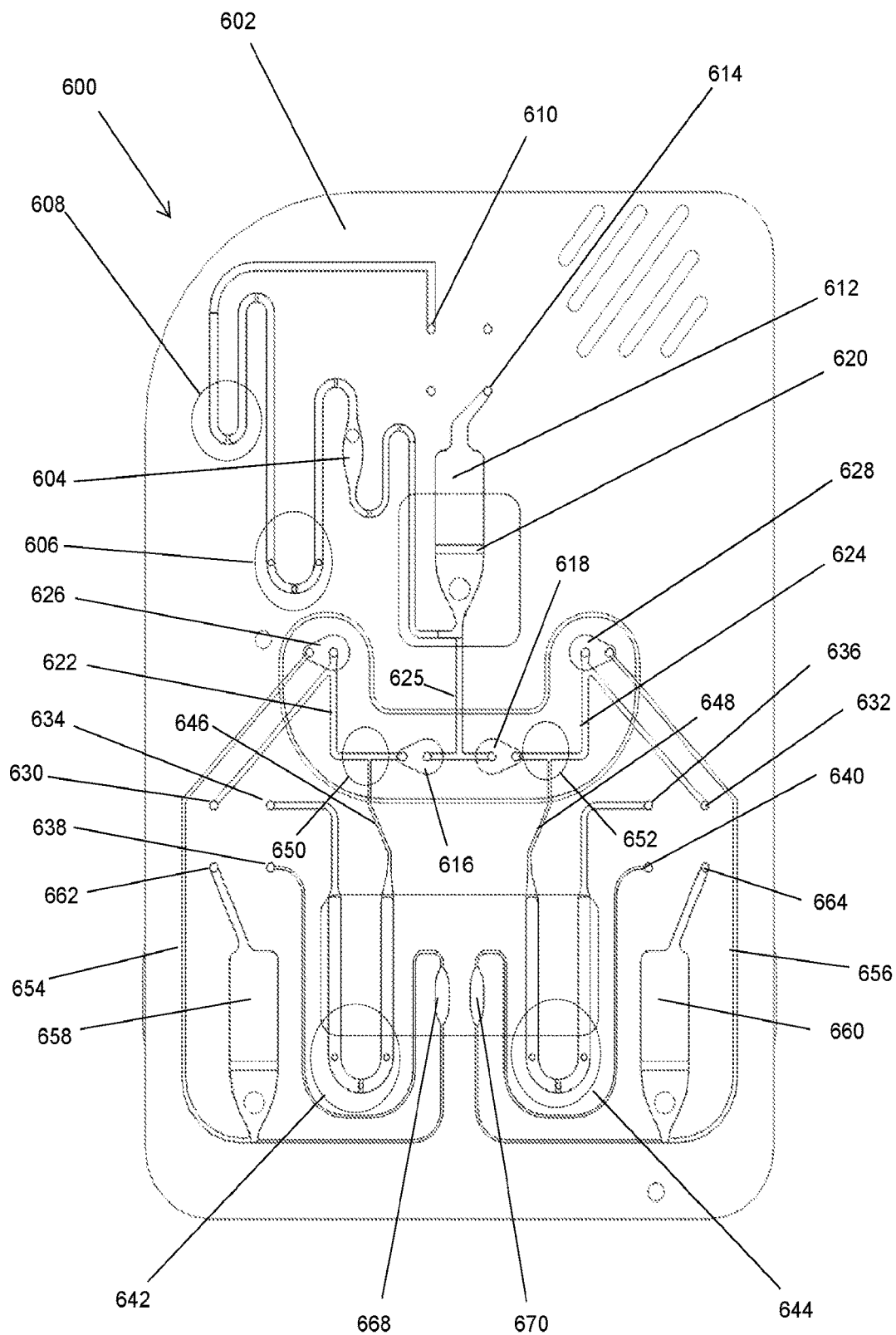
FIG. 6 illustrates the design and operation of a cartridge embodiment that includes amplification of two target polynucleotides in a mixing chamber followed by metering two portions of sample fluid (i.e. the product of the amplification reaction) to separate secondary mixing chambers for mixing with detection reagents. The detection reaction mixture is then drawn into separate detection chambers for separately detecting the target polynucleotides.

FIG. 6 illustrates a cartridge configured to amplify two polynucleotides from a single sample which, after amplification, is separated into two metering chambers for detection in separate detection chambers. Cartridge (600) has in planar body (602) in which are disposed sample chamber (604) to which sample is added. In this embodiment, planar body (602) also comprises upstream of sample chamber (604) reagent chambers (606) and (608) in series both of which are connected to and in fluid communication with port (610). Reagent chamber (608) is optional and whether it is employed depends of the particular bioassay being performed. In some embodiments, reagent chamber (606) contains amplification reagents, for example, for isothermal amplification (via LAMP). In one application, after sample or sample fluid is loaded into sample chamber (604), pressure is applied to vent (610) to drive the sample and amplification reagents to mixing chamber (612) (with vent (614) open and valves (616) and (618) closed). Mixing chamber (612) is shown with wax layer (620) for suppressing bubble formation. In this embodiment, target polynucleotides in the sample are amplified in mixing chamber (612) after which the amplification product is forced into metering chambers (622) and (624) by application of pressure to vent (614) with valves (616) and (618) open, valves (626) and (628) closed and vents (630) and (632) open. Thus, in this embodiment, the amplified polynucleotides from the sample are the samples for the detection reactions and passage (625) may be viewed as a first conduit in accordance with the present invention. After metering chambers (622) and (624) are loaded, valves (616) and (618) are closed, valves (626) and (628) are opened, vents (630) and (632) are closed, vents (638) and (640) are closed, vents (662) and (664) are open, and pressure is applied to vents (634) and (636). This drives detection reagents (for example, CRISPR-based detection reagents) of reagent chambers (642) and (644) through passages (646) and (648), through junctions (650) and (652), through open valves (626) and (628), through passages (654) and (656) and into mixing chambers (658) and (660). After mixing, the resulting reaction mixtures are drawn into detection chambers (668) and (670) by closing valves (626) and (628), opening vents (662) and (664) and applying vacuum to vents (638) and (640). (Alternatively, after mixing, the resulting reaction mixture may be driven into detection chambers (668) and (670) by closing valves (626) and (628), applying pressure to vents (662) and (664) and opening vents (638) and (640).

Manufacture of Cartridges and Appliances

Figure 4A:
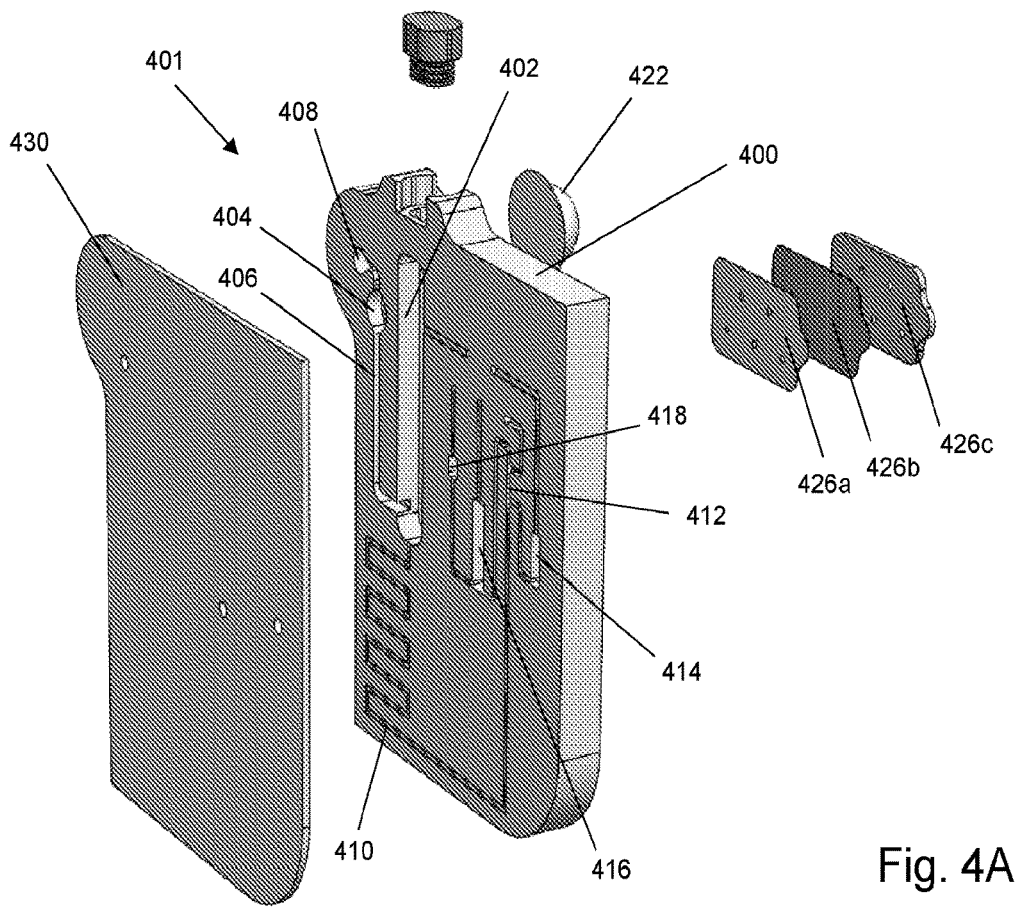
FIGS. 4A and 4B illustrate front (4A) and rear (4B) blow-up views of an embodiment of the invention for performing an isothermal nucleic acid detection assay on a viral sample.
Figure 4B:
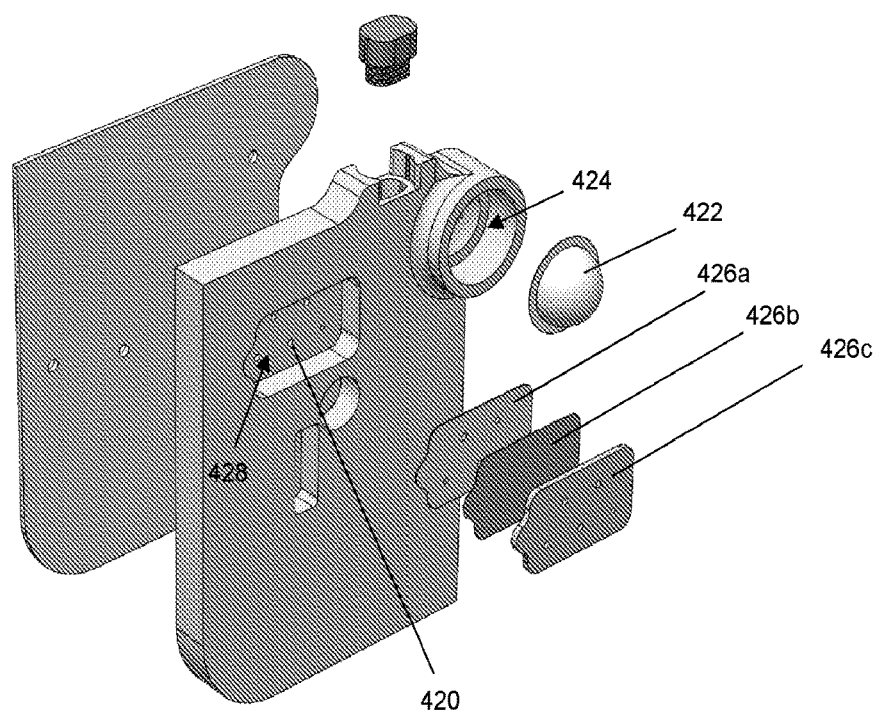

Body (e.g. 202, FIG. 2A) of cartridge (200) may comprise, and the elements described above, such as, chambers and passages, may be formed in, a wide variety of materials well-known in the microfluidics field, such as, silicon, glass, plastic, or the like, e.g. Ren et al, Acc. Chem. Res., 46(11): 2396-2406 (2013). That is, devices of the invention may be fabricated as microfluidics devices using well-known techniques and methodologies of the microfluidic field. In some embodiments, body (202) comprises a plastic, such as, polystyrene, polyethylenetetraphthalate glycol, polyethylene terephthalate, polymethylmethacrylate, polyvinylchloride, polycarbonate, thermo plastic elastomer or the like. Devices of the invention may be fabricated with or in plastic using well-known techniques including, but not limited to, hot embossing, injection molding, laser cutting, milling, etching, 3D printing, or the like. Guidance in the selection of plastics and fabrication methodologies may be found in the following references: Becker et al, Talanta, 56: 267-287 (2002); Fiorini et al, Biotechniques, 38(3): 429-446 (2005); Bjornson et al, U.S. Pat. No. 6,803,019; Soane et al, U.S. Pat. No. 6,176,962; Schaevitz et al, U.S. Pat. No. 6,908,594; Neyer et al, U.S. Pat. No. 6,838,156; and the like, which references are incorporated herein by reference. Appliances for use with cartridges of the invention may be constructed using conventional engineering design principles and materials, e.g. as described in Moore (cited above). FIGS. 4A and 4B show a blow-up view of an embodiment of cartridge (401) from a front view (4A) and rear view (4B). Body (400) may be produced by injection molding techniques to produce sample chamber (402), inhibitor chamber (404), passage (406) connecting lysis buffer chamber (408) and inhibitor chamber (404) to sample chamber (402), first conduit (410), metering chamber (412), reagent chamber (414), mixing chamber (416), detection chamber (418), and vent ports 1-5 (420). Blister pouch (422) is inserted into cavity (424) and membranes and elastic layers (426a-c) are inserted into cavity (428) to form a liquid barrier and mechanism for opening and closing the vent ports, for example, as disclosed by Chen et al, Biomed. Microdevices, 12(4): 705-719 (2010). Plate (430) is fixed to front (432) of body (400) to complete the formation of the various chambers and passages of cartridge (401).

Figure 4C:
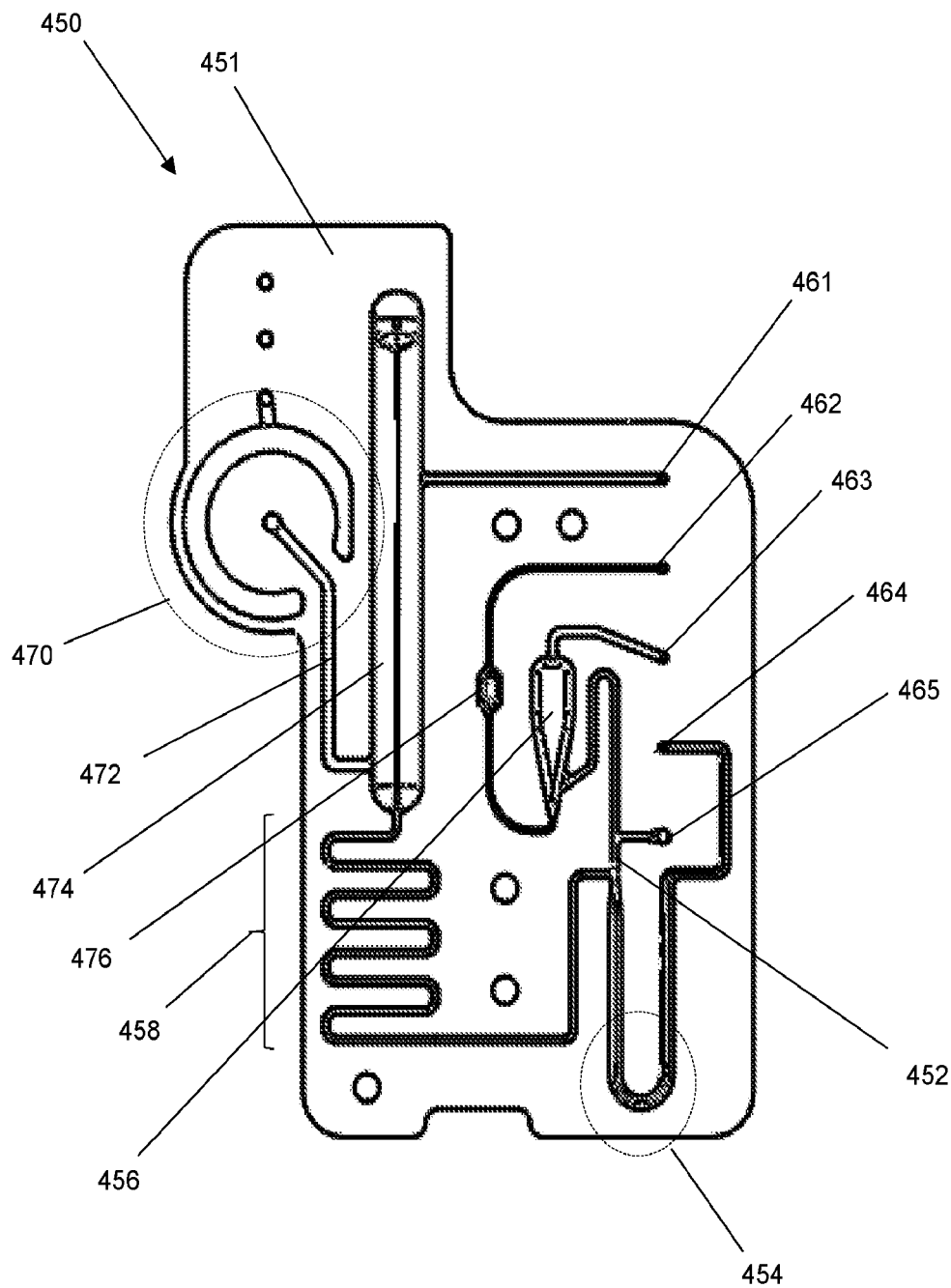
FIGS. 4C and 4D illustrate front (4A) and rear (4B) blow-up views of an embodiment of the invention for performing an isothermal nucleic acid detection assay on a viral sample.
Figure 4D:
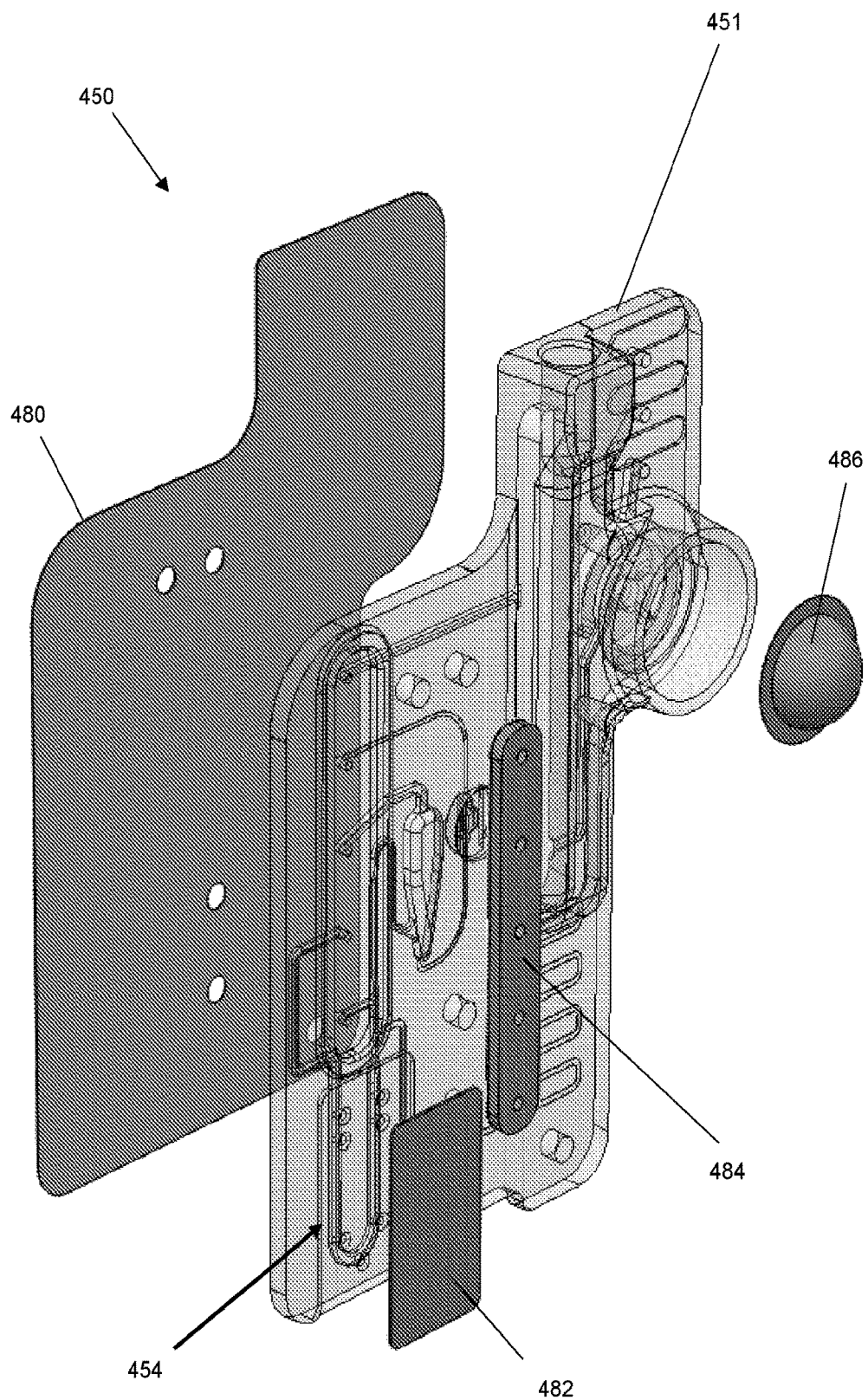

FIG. 4C illustrates a design of a cartridge that does not use gravity to distribute reagents. Planar body (451) of cartridge (450) comprises lysis chamber (470) (showing cartridge feature where blister pack (or pouch) inserts), passage (472) connecting lysis chamber (470 to sample chamber (474), first conduit (458) showing in this example a serpentine path for increasing fluid resistance (discussed above), metering chamber (452), reagent chamber (454) formed in a bend in a passage in which multiple assay reagents may be disposed in different segments of the passage isolated by wax barriers (not shown), mixing chamber (456), and vent ports 1, 2, 3, 4 and 5 (461, 462, 463, 464 and 465, respectively). As above, planar body (451) may be fabricated using conventional injection molding techniques. FIG. 4D illustrates how a cartridge is assembled by adhering cover (480) to a top side of planar body (451), cover (482) over reagent chamber (454) on the obverse side of planar body (451) (after loading assay reagents), elastic cover (484) over vent ports 1-5, and insertion of blister pouch (486). The above part may be assembled using conventional adhesives.

Bioassays

A wide variety of bioassays may be performed in cartridges designed and manufactured in accordance with the invention. In some embodiments, bioassays implemented with the invention are nucleic acid assays, and particularly nucleic acid assays that employ isothermal amplification of one or more target polynucleotides. Isothermal amplification is advantageous because the added components required for thermal cycling, possibly in a separate chamber, is avoided. Many isothermal amplification techniques may be used with the invention including, but not limited to, Nucleic acid sequence-based amplification (NASBA), transcription mediated amplification (TMA), self-sustained sequence replication (3SR), signal-mediated amplification of RNA technology (SMART), strand displacement amplification (SDA), rolling circle amplification (RCA), loop-mediated isothermal amplification of DNA (LAMP), isothermal multiple displacement amplification (TMDA), helicase dependent amplification (HDA), single primer isothermal amplification (SPIA), circular helicase-dependent amplification (cHDA), recombinase-polymerase amplification (RPA), CRISPR-based nucleic acid detection, and the like, e.g. Karami et al, J. Global Infect. Dis., 3(3): 293-302 (2011); Gill et al, Nucleosides, Nucleotides & Nucleic Acids, 27: 224-243 (2008); Wang et al, U.S. Pat. No. 8,673,567; Notomi et al, Nucleic Acids Research, 28(12): e63 (2000); Notomi et al, U.S. Pat. No. 6,410,278; Burns et al, U.S. Pat. No. 6,379,929; Pack et al, U.S. patent publication 2008/0182312; Armes et al, U.S. Pat. No. 7,485,428; Agrawal et al, medRxiv, https://doi.org/10.1101/2020.12.14.20247874 (published Apr. 4, 2021); which references are incorporated by reference. In one embodiment, cartridges of the invention perform a LAMP isothermal amplification. In such embodiments, one or more reagent chambers comprise a DNA polymerase, a primer set for a target polynucleotide, and deoxynucleoside triphosphates (dNTPs). In a further embodiment for detecting RNA target biomolecules, the one or more reagent chambers further contain a reverse transcriptase. In some embodiments, a LAMP amplification product is detected optically. In some embodiments, such optical detection is based on an optical measure of the turbidity of the LAMP amplification mixture, e.g. magnitude of light transmission, magnitude of light scatter, or the like, Zhu et al, ACS Omega, 5: 5421-5428 (2020). In other embodiments, a LAMP amplification product is detected colorimetrically, e.g. Goto et al, Biotechniques, 46(3): 167-172 (2009). In still other embodiments, a LAMP amplification product is measured by fluorescence, e.g. Gadkar et al, Scientific Reports, 8:5548 (2018); Hardinge et al, Scientific Reports, 9:7400 (2019); or the like, wherein fluorescence intensity may be monotonically related to amount of target polynucleotide in a sample. In some embodiments, an intercalating fluorescent DNA dye is used to measure the quantity of LAMP amplification product, e.g. Oscorbin et al, Biotechniques, 61(1): 20-25 (2016); Quyen et al, Frontiers Microbiol., 10: 2234 (2019); or the like.

Samples and Lysis Buffers

Cartridges and appliances of the invention may be adapted to detect and measure biomolecules in a wide variety of biological samples. Typically a lysis buffer or lysis condition is selected to facilitate access of the biomolecules of interest in a sample to reagents of a bioassay. Lysis may be accomplished or facilitated mechanically, chemically, electrically or thermally. Determining the best lysis buffer for a particular sample type and biomolecule can be accomplished by those of ordinary skill, for example, as exemplified by the following references: Kim et al, Integrative Biology, 1: 574-586 (2009); Svec et al, Frontiers in Oncology, 3: 1-11 (2013); E. H. Lennette (ed.), Laboratory Diagnosis of Viral Infections, second edition (Marcel Dekker, Inc., New York, 1992); Fiechtner et al, U.S. patent Ser. No. 10/520,498; which are hereby incorporated by reference. In some embodiments, a reaction mixture for a bioassay may comprise a lysis buffer to facilitate access of the assay reagents to target nucleic acids. Lysing conditions may vary widely and may be based on the action of heat, detergent, protease, alkaline, chaotropic agents or combinations of such factors. Whenever biomolecules of interest are viral polynucleotides in a sample comprising viral particles shed into a biological fluid, e.g. saliva, in some embodiments, a lysis buffer may comprise agents to disrupt the viral protein coat and to protect the release nucleic acids, such as RNA. In some embodiments, a lysis buffer may comprise a chaotropic agent, a detergent and a nuclease inhibitor. Exemplary chaotropic agents include guanidinium thiocyanate and guanidinium chloride. Exemplary lysis buffers for use with RNA viruses may be obtained commercially, e.g. Qiagen ATL (25-50% Guanidinium Thiocyanate (GITC) and 1-10% sodium dodecyl sulfate), VXL (25-50% GITC, 2.5-10% Triton-X-100), and AVL (50-70% GITC).

While the present invention has been described with reference to several particular example embodiments, those skilled in the art will recognize that many changes may be made thereto without departing from the spirit and scope of the present invention. The present invention is applicable to a variety of implementations in addition to those discussed above.

Definitions

"Amplicon" means the product of a polynucleotide amplification reaction; that is, a clonal population of polynucleotides, which may be single stranded or double stranded, which are replicated from one or more starting sequences. "Amplifying" means producing an amplicon by carrying out an amplification reaction. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Bioassay reagents" or "assay reagents," which are used interchangeably herein, mean reagents used to perform an analytical reaction on a cartridge of the invention. Such reagents may include enzymes, enzyme co-factors, primers, waxes for bubble suppression, salts, buffers, solvents, agents to modify the secondary structure of analytes, labels (such as fluorescent dyes or fluorescently labeled oligonucleotides), lysis buffers, and the like, which make up a reaction mixture. In some embodiments, assay reagents include reagents for carrying out an isothermal amplification of one or more target polynucleotides.

"Dried reagents" mean assay reagents, such as buffers, salts, active compounds, such as enzymes, co-factors, and the like, or binding compounds, such as antibodies, aptamers, or the like, that are provided in a dehydrated formulation for the purpose of improved shelf-life, ease of transport and handling, improved storage, and the like. The nature, composition, and method of producing dried reagents vary widely and the formulation and production of such materials is well-known to those of ordinary skill in the art as evidenced by the following references that are incorporated by reference: Franks et al, U.S. Pat. No. 5,098,893; Cole, U.S. Pat. No. 5,102,788; Shen et al, U.S. Pat. No. 5,556,771; Treml et al, U.S. Pat. No. 5,763,157; De Rosier et al, U.S. Pat. No. 6,294,365; Buhl et al, U.S. Pat. No. 5,413,732; McMillan, U.S. patent publication 2006/0068398; McMillan et al, U.S. patent publication 2006/0068399; Schwegman et la (2005), Pharm. Dev. Technol., 10: 151-173; Nail et al (2002), Pharm. Biotechnol., 14: 281-360; and the like. Dried reagents include, but are not limited to, solid and/or semi-solid particulates, powders, tablets, crystals, capsules and the like, that are manufactured in a variety of ways. In one aspect, dried reagents are lyophilized particulates. Lyophilized particulates may have uniform compositions, wherein each particulate has the same composition, or they may have different compositions, such that two or more different kinds of lyophilized particulates having different compositions are mixed together. Lyophilized particulates can contain reagents for all or part of a wide variety of assays and biochemical reactions, including immunoassays, enzyme-based assays, enzyme substrate assays, and the like. In one aspect, a lyophilized particulate of the invention comprises an excipient and at least one reagent of an assay. Lyophilized particulates may be manufactured in predetermined sizes and shapes, which may be determined by the type of assay being conducted, desired reaction volume, desired speed of dissolution, and the like. In some embodiments, lyophilized particulates are provided in a size such that they are mobile within whatever chamber they are disposed in. Dried reagents may include excipients, which are usually inert substances added to a material in order to confer a suitable consistency or form to the material. A large number of excipients are known to those of skill in the art and can comprise a number of different chemical structures. Examples of excipients, which may be used in the present invention, include carbohydrates, such as sucrose, glucose, trehalose, melezitose, dextran, and mannitol; proteins such as BSA, gelatin, and collagen; and polymers such as PEG and polyvinyl pyrrolidone (PVP). The total amount of excipient in the lyophilized particulate may comprise either single or multiple compounds. In some embodiments, the type of excipient is a factor in controlling the amount of hygroscopy of a dried reagent. Lowering hygroscopy can enhance the a dried reagent's integrity and cryoprotectant abilities. However, removing all water from such a composition would have deleterious effects on those reaction components, proteins for example, that require certain amounts of bound water in order to maintain proper conformations.

"Isothermal amplification" in reference to an assay to detect or quantify a target nucleic acid or polynucleotide means a method of replicating a target nucleic acid without a requirement of thermal cycling. That is, without a requirement of subjecting a reaction mixture to cycles of different temperatures in order to melt target nucleic acid strands, anneal primers and provide for extension conditions for a DNA polymerase. An isothermal amplification is typically performed at a predetermined temperature.

"Microfluidics" device or "nanofluidics" device, used interchangeably herein, each means an integrated system for capturing, moving, mixing, dispensing or analyzing small volumes of fluid, including samples (which, in turn, may contain or comprise cellular or molecular analytes of interest), reagents, dilutants, buffers, or the like. Generally, reference to "microfluidics" and "nanofluidics" denotes different scales in the size of devices and volumes of fluids handled. In some embodiments, features of a microfluidic device have cross-sectional dimensions of less than a few hundred square micrometers and have passages, or channels, with capillary dimensions, e.g. having maximal cross-sectional dimensions of from about 1-2 mm to about 0.1 µm. In some embodiments, microfluidics devices have volume capacities in the range of from 100 µL to a few nL, e.g. 10-100 nL or in the range of from 100 µL to 1 µL. Dimensions of corresponding features, or structures, in nanofluidics devices are typically from 1 to 3 orders of magnitude less than those for microfluidics devices. One skilled in the art would know from the circumstances of a particular application which dimensionality would be pertinent. In some embodiments, microfluidic or nanofluidic devices have one or more chambers, ports, and channels that are interconnected and in fluid communication and that are designed for carrying out one or more analytical reactions or processes, either alone or in cooperation with an appliance or instrument that provides support functions, such as sample introduction, fluid and/or reagent driving means, such as positive or negative pressure, acoustical energy, or the like, temperature control, detection systems, data collection and/or integration systems, and the like. In some embodiments, microfluidics and nanofluidics devices may further include valves, pumps, filters and specialized functional coatings on interior walls, e.g. to prevent adsorption of sample components or reactants, facilitate reagent movement by electroosmosis, or the like. Such devices may be fabricated as an integrated device in a solid substrate, which may be glass, plastic, or other solid polymeric materials, and may have a planar format for ease of detecting and monitoring sample and reagent movement, especially via optical or electrochemical methods. In some embodiments, such devices are disposable after a single use. In some embodiments, microfluidic and nanofluidic devices include devices that form and control the movement, mixing, dispensing and analysis of droplets, such as, aqueous droplets immersed in an immiscible fluid, such as a light oil. The fabrication and operation of microfluidics and nanofluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128;

5,498,392; Sia et al, Electrophoresis, 24: 3563-3576 (2003); Unger et al, Science, 288: 113-116 (2000); Enzelberger et al, U.S. Pat. No. 6,960,437; Cao, "Nanostructures & Nanomaterials: Synthesis, Properties & Applications," (Imperial College Press, London, 2004); Haeberle et al, LabChip, 7: 1094-1110 (2007); Cheng et al, Biochip Technology (CRC Press, 2001); and the like.

"NASBA" or "Nucleic acid sequence-based amplification" is an amplification reaction based on the simultaneous activity of a reverse transcriptase (usually avian myeloblastosis virus (AMV) reverse transcriptase), an RNase H, and an RNA polymerase (usually T7 RNA polymerase) that uses two oligonucleotide primers, and which under conventional conditions can amplify a target sequence by a factor in the range of 109 to 1012 in 90 to 120 minutes. In a NASBA reaction, nucleic acids are a template for the amplification reaction only if they are single stranded and contain a primer binding site. Because NASBA is isothermal (usually carried out at 41° C. with the above enzymes), specific amplification of single stranded RNA may be accomplished if denaturation of double stranded DNA is prevented in the sample preparation procedure. That is, it is possible to detect a single stranded RNA target in a double stranded DNA background without getting false positive results caused by complex genomic DNA, in contrast with other techniques, such as RT-PCR. By using fluorescent indicators compatible with the reaction, such as molecular beacons, NASBAs may be carried out with real-time detection of the amplicon. Molecular beacons are stem-and-loop-structured oligonucleotides with a fluorescent label at one end and a quencher at the other end, e.g. 5'-fluorescein and 3'-(4-(dimethylamino)phenyl)azo) benzoic acid (i.e., 3'-DABCYL), as disclosed by Tyagi and Kramer (cited above). An exemplary molecular beacon may have complementary stem strands of six nucleotides, e.g. 4 G's or C's and 2 A's or T's, and a target-specific loop of about 20 nucleotides, so that the molecular beacon can form a stable hybrid with a target sequence at reaction temperature, e.g. 41° C. A typical NASBA reaction mix is 80 mM Tris-HCl [pH 8.5], 24 mM MgCl2, 140 mM KCl, 1.0 mM DTT, 2.0 mM of each dNTP, 4.0 mM each of ATP, UTP and CTP, 3.0 mM GTP, and 1.0 mM ITP in 30% DMSO. Primer concentration is 0.1 µM and molecular beacon concentration is 40 nM. Enzyme mix is 375 sorbitol, 2.1 µg BSA, 0.08 U RNase H, 32 U T7 RNA polymerase, and 6.4 U AMV reverse transcriptase. A reaction may comprise 5 µL sample, 10 µL NASBA reaction mix, and 5 µL enzyme mix, for a total reaction volume of 20 µL. Further guidance for carrying out real-time NASBA reactions is disclosed in the following references that are incorporated by reference: Polstra et al, BMC Infectious Diseases, 2: 18 (2002); Leone et al, Nucleic Acids Research, 26: 2150-2155 (1998); Gulliksen et al, Anal. Chem., 76: 9-14 (2004); Weusten et al, Nucleic Acids Research, 30(6) e26 (2002); Deiman et al, Mol. Biotechnol., 20: 163-179 (2002). Nested NASBA reactions are carried out similarly to nested PCRs; namely, the amplicon of a first NASBA reaction becomes the sample for a second NASBA reaction using a new set of primers, at least one of which binds to an interior location of the first amplicon.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference:

Dieffenbach, editor, PCR Primer: A Laboratory Manual, 2nd Edition (Cold Spring Harbor Press, New York, 2003).

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Sample" (or "biological sample" which is used synonymously) means a quantity of material from a biological, environmental, medical, or patient source in which detection or measurement of target biomolecule, such as a target nucleic acids, is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, such as, fluids from nasal or other schwabs, as well as liquid and solid food and feed products and ingredients such as dairy items, vegetables, meat and meat by-products, and waste. Biological samples may include materials taken from a patient including, but not limited to cultures, blood, saliva, tears, sweat, urine, cerebral spinal fluid, pleural fluid, milk, lymph, sputum, semen, needle aspirates, and the like. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

What is claimed is:

1. A device for performing a bioassay on a biological sample to determine the presence or quantity of one or more target polynucleotides when connected to an appliance that provides pressure and vacuum sources and a detection station, the device comprising:

a planar body comprising a sample chamber, a first conduit, at least one reagent chamber, at least one metering chamber, at least one mixing chamber and at least one detection chamber, wherein:

the sample chamber has a first inlet accepting a biological sample or a sample fluid containing a biological sample, a vent port allowing the passage of air but not liquid, and an outlet connected to the first conduit, wherein the vent port is capable of being sealingly connected to a valve in the appliance;

the metering chamber (a) connected to and in fluid communication with a reagent chamber, (b) connected to and in fluid communication with the outlet of the sample chamber through the first conduit, (c) connected to a metering vent port, and (d) connected to and in fluid communication with a mixing chamber conduit, wherein the metering vent port is capable of being sealingly connected to a valve in the appliance;

the reagent chamber capable of containing assay reagents, the reagent chamber being connected to the metering chamber by a passage and connected to a reagent vent port allowing the passage of air but not liquid, wherein the reagent vent port is capable of being sealingly connected to a valve and pump in the appliance so that the reagent port is capable of accepting air pressure for forcing the assay reagents into the metering chamber;

the mixing chamber for mixing the biological sample or sample fluid with the assay reagents, the mixing chamber having a top and a bottom and being in fluid communication with the metering chamber by a passage connecting the bottom of the mixing chamber to the metering chamber, the mixing chamber being connected at its top to a mixing vent port that allows the passage of air but not liquid, wherein the mixing vent port is capable of being sealingly connected to a valve in the appliance, wherein the mixing chamber or the reagent chamber or both chambers contain a predetermined quantity of wax having a melting temperature such that the wax forms a bubble-preventing layer on a reaction mixture whenever the mixing chamber is above the melting temperature; and the detection chamber is in fluid communication with the mixing chamber by a passage connecting the detection chamber to the bottom of the mixing chamber, and the detection chamber is connected at its top to a detection vent port that allows the passage of air but not liquid, wherein the detection vent port is capable of being sealingly connected to a valve and vacuum source in the appliance so that the detection port is capable of accepting a vacuum for drawing the mixture of assay reagents and biological sample or sample fluid into the detection chamber from the mixing chamber.

2. The device of claim 1 wherein said assay reagents are immobilized in said reagent chamber by wax barriers comprising said wax, and wherein said assay reagents and said wax of the wax barriers are capable of being released upon heating said reagent chamber to a temperature above said melting temperature of said wax.

3. The device of claim 1 wherein said passage connecting said detection chamber to said bottom of said mixing chamber comprises an amplification chamber for said target polynucleotides.

4. The device of claim 3 wherein said amplification chamber is configured to produce a predetermined temperature in the range of from 55° C. to 70° C.

5. The device of claim 3 wherein said amplification chamber is configured to produce a predetermined temperature in the range of from 30° C. to 60° C.

6. A device for performing a bioassay for one or more target polynucleotides comprising:

a sample chamber comprising a first inlet for accepting a biological sample, a vent port allowing the passage of air but not liquid, and an outlet connected to a first conduit;

a metering chamber (a) connected to and in fluid communication with a reagent chamber, (b) connected to and in fluid communication with the outlet of the sample chamber through the first conduit, (c) connected to a metering vent port, and (d) connected to and in fluid communication with a mixing chamber conduit;

a reagent chamber capable of containing assay reagents, the reagent chamber being connected to the metering chamber by a passage and connected to a reagent vent port allowing the passage of air but not liquid;

a mixing chamber for mixing the biological sample with the assay reagents, the mixing chamber having a top and a bottom and being in fluid communication with the metering chamber by a passage connecting the bottom of the mixing chamber to the metering chamber, the mixing chamber being connected at its top to a mixing vent port that allows the passage of air but not liquid, wherein the mixing chamber or the reagent chamber or both chambers contain a predetermined quantity of wax having a melting temperature such that the wax forms a bubble-preventing layer on a reaction mixture whenever the mixing chamber is above the melting temperature; and a detection chamber is in fluid communication with the mixing chamber by a passage connecting the detection chamber to the bottom of the mixing chamber, and the detection chamber is connected at its top to a detection vent port that allows the passage of air but not liquid.

7. The device of claim 6 wherein said passage connecting said detection chamber to said bottom of said mixing chamber comprises an amplification chamber for said target polynucleotides.

8. The device of claim 7 wherein said amplification chamber is configured to produce a predetermined temperature in the range of from 55° C. to 70° C.

9. The device of claim 7 wherein said amplification chamber is configured to produce a predetermined temperature in the range of from 30° C. to 60° C.

10. The device of claim 6 wherein said assay reagents are immobilized in said reagent chamber by wax barriers comprising said wax, and wherein said assay reagents and said wax of the wax barriers are capable of being released upon heating said reagent chamber to a temperature above said melting temperature of said wax.

\* \* \* \* \*